US012751793B2

(12) United States Patent
Annucci

(10) Patent No.: US 12,751,793 B2
(45) Date of Patent: Oct. 6, 2026

(54) SELECTING TOOL HEADS FOR A TOOTH PREPARATION

(71) Applicant: EXOCAD GMBH, Darmstadt (DE)

(72) Inventor: Marco Annucci, Rome (IT)

(73) Assignee: EXOCAD GMBH, Darmstadt (DE)

(*) Notice: Subject to any disclaimer, the term of this patent is extended or adjusted under 35 U.S.C. 154(b) by 202 days.

(21) Appl. No.: 18/734,353

(22) Filed: Jun. 5, 2024

(65) Prior Publication Data

US 2025/0375263 A1 Dec. 11, 2025

(51) Int. Cl.

| | |
|---|---|
| ***A61C 1/08*** | (2006.01) |
| ***A61C 3/02*** | (2006.01) |
| ***A61C 9/00*** | (2006.01) |
| ***G06F 30/20*** | (2020.01) |
| ***G16H 20/40*** | (2018.01) |

(52) U.S. Cl.

CPC ................ *A61C 3/02* (2013.01); *A61C 1/082* (2013.01); *A61C 9/0046* (2013.01); *G06F 30/20* (2020.01); *G16H 20/40* (2018.01)

(58) Field of Classification Search

CPC ................................ A61C 1/082; G16H 20/40

See application file for complete search history.

(56) References Cited

U.S. PATENT DOCUMENTS

| | | | | |
|---|---|---|---|---|
| 10,052,171 | B1 | 8/2018 | Almalki | |
| 2021/0000575 | A1* | 1/2021 | Zhang ..................... | B22F 10/66 |
| 2024/0130834 | A1 | 4/2024 | Kopelman | |

FOREIGN PATENT DOCUMENTS

| | | |
|---|---|---|
| CN | 111775440 B | 2/2022 |

* cited by examiner

*Primary Examiner* — Matthew D Salvucci

(74) *Attorney, Agent, or Firm* — Perry + Currier Inc.

(57) ABSTRACT

Disclosed is a computer-implemented method for selecting tool heads for a tooth preparation comprising a removal of tooth material. The method comprises receiving a three-dimensional digital initial tooth model and a three-dimensional digital target tooth model. Definitions of tool heads of a plurality of tool heads of a plurality of tool kits are received. It is checked for different combinations and sequences of usage of the tool heads, whether one or more preparation criteria are satisfied. A selection and sequence of usage of tool heads is determined for the tooth preparation satisfying the one or more preparation criteria. A result of a simulation of the tooth preparation is output comprising a definition of the selection and sequence of usage.

18 Claims, 16 Drawing Sheets

SELECTING TOOL HEADS FOR A TOOTH PREPARATION

FIELD OF THE INVENTION

The invention relates to the field of dental technology, in particular to a method for selecting tool heads for a tooth preparation comprising a removal of tooth material.

BACKGROUND

Dentists use tool kits comprising different combinations of tool heads for preparing teeth. However, since no two teeth are alike every preparation of a tooth may be different. In addition, there are different types of preparation, e.g., depending on the type of dental protheses, for which the tooth is to be prepared.

Thus, predefined kits may often not provide an optimal combination of tool heads for executing a particular preparation of a particular tooth.

SUMMARY OF THE INVENTION

It is an objective to provide for a method, a program product, and a computer device for selecting tool heads for a tooth preparation comprising a removal of tooth material. The objectives underlying the invention are solved by the features of the independent claims.

In one aspect a computer-implemented method is disclosed for selecting tool heads for a tooth preparation comprising a removal of tooth material. The method comprises receiving a three-dimensional digital initial tooth model descriptive of one or more current states of one or more teeth to be prepared.

A three-dimensional digital target tooth model descriptive of one or more target states of the respective one or more teeth to be prepared is received. The one or more target states are to be achieved starting from the one or more current states by preparing the one or more teeth to be prepared comprising the removal of the tooth material from the respective teeth. Definitions of tool heads of a plurality of tool heads of a plurality of tool kits defining features of the tool heads of the plurality of tool heads are received.

It is checked, using the defined features of the tool heads of the plurality of tool heads, for different combinations and sequences of usage of the tool heads of the plurality of tool heads, whether one or more preparation criteria are satisfied.

A selection of tool heads from the plurality of tool heads and a sequence of usage of the tool heads of the selection for the tooth preparation satisfying the one or more preparation criteria are determined. The determining comprises executing a simulation of the tooth preparation using the tool heads of the selection according to the sequence of usage of the tool heads of the selection. The simulation is executed using the defined features of the respective tool heads of the selection. A result of the simulation is output comprising a definition of the selection of tool heads and the sequence of usage of the tool heads of the selection.

The plurality of tool kits may, e.g., be a plurality of tool kits available for usage for the tooth preparation. Each of the tool kits may, e.g., comprise a combination of tool heads for executing the tool preparation. The definitions of tool heads may, e.g., define features of the tool heads available for usage.

Examples may have the beneficial effect that a selection of tool heads for a tooth preparation comprising a removal of tooth material may be provided. The selection may be determined such that the selection satisfies one or more preparation criteria, i.e., such that a tooth preparation executed using the tool heads of the selection according to the sequence for usage determined for this selection satisfies the one or more preparation criteria.

For example, none of the tool kits, i.e., none of the predefined combinations of tool heads provided by the individual tool kits, may be configured to satisfies one or more preparation criteria. Examples may enable a determining of a selection of tool heads comprising a combination tool heads from different tool kits, which satisfies the one or more preparation criteria.

For example, one or more of the one or more preparation criteria may require that one or more features of the tooth preparation are optimized, e.g., that a preparation time is minimized and/or that a precision of a preparation is maximized. Examples may enable a determining of a selection of tool heads comprising a combination of tool heads from different tool kits, for which the respective one or more features of the tooth preparation are optimized. For example, a preparation time using the selection of tool heads may be short than any other preparation time resulting from using any of the predefined tool kits. For example, a precision of the tooth preparation using the selection of tool heads may be higher than any other precision resulting from using any of the predefined tool kits.

The precision criterion may, e.g., result in a requirement to use a tool head with a certain shape to be able to achieve a certain shape of the preparation. The shape of the preparation may, e.g., be a negative of the shape of the tool head. For example, the preparation to be achieved as defined by the three-dimensional digital target tooth model may define a specific form of a margin line for the preparation. Achieving this form may require a tool head with a suitable form. For example, the selection of tool heads may comprise one or more tool heads from one or more of the tool kits for performing a basic preparation, e.g., in order to save preparation time, and one or more other tool heads from one or more other tool kits for a finishing of the preparation, e.g., for forming a margin line of the preparation with a specific predefined form.

The result of the simulation may, e.g., at least comprise a definition of the selection of tool heads and the sequence of usage of the tool heads of the selection. The simulation result may, e.g., further comprise a definition of preparation trajectories preparation trajectories for moving the tool heads of the selection according to the sequence of usage of the tool heads of the selection through the teeth to be prepared.

The simulation result may, e.g., further comprise a definition of intermediate states of the tooth preparation to be achieved using the tool heads of the selection according to the sequence of usage of the tool heads of the selection. For example, for each tool head of the selection an intermediate state of the preparation may be defined. The intermediate state may define, which state of the preparation is to be achieved using the respective tool head.

The sequence of intermediate states of the preparation may thus illustrate a successive evolution of the preparation tool head per tool head following the sequence of usage of the respective tool heads.

The three-dimensional digital target tooth model may be defined starting with three-dimensional digital initial tooth model. For each of the one or more current states of the one or more teeth to be prepared according to the three-dimensional digital initial tooth model, section of the respective tooth may be identified, which have to be removed. These sections to be removed may, e.g., comprise damaged tooth sections, unsupported tooth sections, tooth sections to be removed for providing sufficient space to receive a restoration, and/or tooth section comprising an undercut.

Furthermore, the removal of tooth material may be determined such that the resulting target states comprise smooth transitions between different section of the prepared teeth. Furthermore, the removal of tooth material may be determined such that the resulting target states comprise proportion surfaces resulting from the tooth preparation with predefined inclinations, e.g., relative to an occlusal direction, which ensure a sufficient support for the restorations arranged in and/or on the prepared teeth.

For example, the method further comprises receiving definition of a restoration or a restoration method, for which the one or more teeth are to be preparate. A restoration may influence the form of the preparation to be achieved. For example, a prepared tooth may be required to provide sufficient space for receiving a restoration with a predefined minimum thickness required, e.g., for a sufficient stability of the restoration.

The three-dimensional digital initial tooth model may, e.g., be a model provided using scan data of the respective one or more teeth. The method may, e.g., further comprise generating the three-dimensional digital initial tooth model using scan data. The method may, e.g., further comprise receiving the scan data used for generating the three-dimensional digital initial tooth model. The method may, e.g., further comprise acquiring the respective scan data using one or more scanners.

The scan data may, e.g., be acquired using an optical scanner. The scan may be a direct scan of the one or more teeth, e.g., an intraoral scan within a patient's oral cavity. Alternatively or additionally, an indirect scan of the one or more teeth may be used to acquire the scan data. For example, a dental impression of the one or more teeth or a dental model of the respective one or more teeth, like a plaster model, may be scanned.

The three-dimensional digital initial tooth model may, e.g., be provided in form of a three-dimensional digital dentition model of a dentition comprising the one or more tooth to be prepared. The three-dimensional digital dentition model of the dentition may, e.g., be provided using scan data of the dentition. The one or more teeth to be prepared may be identified within the three-dimensional digital dentition model of the dentition using segmentation.

The scan data of the dentition may be acquired using a scanner, e.g., an optical scanner. The scan may be a direct scan of the dentition, e.g., an intraoral scan within a patient's oral cavity. Alternatively or additionally, an indirect scan of the dentition may be used to acquire the scan data. For example, a dental impression of the dentition or a dental model of the dentition, like a plaster model, may be scanned.

The three-dimensional digital initial tooth model may be a three-dimensional digital model of one or more current states of one or more teeth to be prepared. It may resemble current states of the one or more teeth, i.e., it may be a digital replica of the respective one or more physical teeth to be prepared. The three-dimensional digital initial tooth model may, in particular, resemble current geometric forms of the one or more teeth to be prepared. The three-dimensional digital initial tooth model may further resemble current positions of the one or more physical teeth to be prepared within the physical dentition. The three-dimensional digital initial tooth model may, e.g., be generated by a computer system executing the method described herein or it may be received from an external source. The external source may, e.g., be a server, like a cloud server, providing the three-dimensional digital tooth model via a network. The external source may, e.g., be a removable storage device providing the three-dimensional digital tooth model via a direct communication connection, e.g., wireless or via a wire.

For identifying damaged sections of the one or more teeth to be prepared, e.g., additional scan data of an X-ray, CT, CBCT and/or near-infrared scan may be used. The information provided by the additional scan data may, e.g., be part of the three-dimensional digital initial tooth model or may be provided in addition to the three-dimensional digital initial tooth model. For example, scan data of an X-ray and/or CBCT scan of the tooth are received. For example, DICOM data of X-ray images and/or CBCT images of the tooth are received. For example, scan data of a near-infrared scan of the tooth are received.

A dental preparation refers to a method by which a tooth is prepared for receiving a dental restoration. With the dental restoration function, integrity, and/or morphology of missing tooth structure may be restored. Furthermore, the morphology of the tooth may also be altered using a dental restoration. The dental restoration may, e.g., be a direct restoration. A direct restoration comprises placing a soft or malleable restorative material onto and/or into the prepared tooth and thereby building up the tooth. The restorative material may then set hard resulting in a restored tooth. The dental restoration may, e.g., be an indirect restoration. An indirect restoration comprising using a dental prothesis, which may be manufactured outside of a patient's mouth and then arranged on the prepared tooth. Indirect restorations may, e.g., comprise inlays, onlays, crowns, bridges, and veneers.

A preparation of a tooth may in general comprises removing tooth material. The respective tooth material or tooth mass may, e.g., be cut away by milling and/or drilling.

The preparing of the tooth may comprise removing damaged sections of the tooth. Damaged sections may, e.g., be due to decay and/or external trauma. The preparing of the tooth may comprise designing a form of the prepared tooth that provide adequate retention for a dental restoration to be arranged on and/or in the prepared tooth.

Restoring one or more teeth may require removing tooth material and preparing the teeth for a placement of restorative material or materials, e.g. in form of a direct or indirect restoration, as well as the placement of this restorative material or materials.

However, an efficiency and/or effectiveness of a dental preparation may depend on the tool heads and/or sequence of usage of these tool heads. Therefore, before executing the actual preparation, it may be required to provide a suitable combination of tool heads for the respective preparation. These tool heads, e.g., milling and/or drilling heads may be configured to be used with a dental handpiece and/or be a robotic device.

A dental handpiece refers to a hand-held, mechanical preparation instrument used to perform a dental preparation procedure, including a removal of tooth material using a tool head inserted into the dental handpiece. The dental handpiece may, e.g., comprise internal mechanical components that initiate a rotational force and provide power to the tool head for removing tooth material.

A robotic device may, e.g., comprise a mechanical movement unit, like a robotic arm, configured to move a mechanical preparation instrument used to perform a dental preparation procedure, including a removal of tooth material using a tool head inserted into the preparation instrument. The preparation instrument may, e.g., comprise internal mechanical components that initiate a rotational force and provide power to the tool head for removing tooth material.

A preparation of a tooth may, e.g. comprise a removal of tooth material to provide space for receiving planned restorative material, to remove damaged tooth sections and/or to remove sections of the tooth that are structurally unsound.

A preparation may, e.g., be an intracoronal preparation. A preparation may, e.g., be an extracoronal preparation. An intracoronal preparation is a preparation, which is configured to hold restorative material within confines of a structure of a crown of a tooth. Examples may comprise all classes of cavity preparations as well as preparations for gold inlays. An intracoronal preparation may also be configured to provide as a female recipient for receiving a male component of a removable partial or full denture. An extracoronal preparation may, e.g., be configured to provide a core or base upon which restorative material may be arranged to bring the tooth into a functional and/or aesthetic target structure. Examples may comprise crowns and onlays, as well as veneers.

For example, a minimum extent of a preparation, i.e., of a removal of tooth material, may, e.g., depend on an extent of damaged sections comprised by a tooth.

Furthermore, an extent of a preparation may, e.g., depend on an extent of unsupported tooth structures comprised by a tooth. When preparing a tooth to receive a restoration, unsupported structures, e.g., unsupported enamel section may be removed to allow for a more stable restoration. While enamel is a very hard substance, it is also rather brittle, which is why unsupported enamel may fracture easily.

Examples may have the beneficial effect that a selection of tool head is provided that enables the teeth tooth to be prepared in an effective and efficient way to achieve desired target state of the preparation as defined by the three-dimensional digital target tooth model. This target state, i.e., the three-dimensional digital target tooth model, may, e.g., depending on a desired treatment.

For example, a step-by-step guide for executing a tooth preparation using tool heads provided by different tool kits may be provided. The step-by-step guide may, e.g., define a sequence of preparation steps as well as a sequence of tool head to be used for the respective preparation steps.

A step-by-step guide may, e.g., define use tool head X of tool kit Y for preparation step N, in order to achieve a desired result. Such a step-by-step guide may be displayed on a graphical user interface. Such a step-by-step guide may be output in form of digital document, e.g., a PDF document.

For example, the result of the simulation may be output in form of a step-by-step guide. For example, the result of the simulation may be output in form of a visualization, e.g., an animation displayed on a graphical user interface illustrating the preparation steps of the preparation and showing how this preparation can be achieved.

Example may, e.g., comprise a selecting of tool heads and/or tool kits comprising a plurality of tool heads each that are available for use. Thus, a plurality of tool heads of a plurality of tool kits available for being selected for a tooth preparation to be executed may be defined. Definitions of tool heads of a plurality of tool heads of a plurality of tool kits defining features of the tool heads of the plurality of tool heads may be compiled.

A tooth restorative treatment may be planned. Planning the tooth restorative treatment may comprise generating the three-dimensional digital target tooth model descriptive of one or more target states of the one or more teeth to be prepared.

A simulation of how the desired preparation of the teeth as defined by the three-dimensional digital target tooth model may be achieved using the tool heads available for the preparation may be executed.

Examples may enable a faster, e.g., a two to three times faster selection of tool heads required for a specific preparation. Alternatively, it may also be indicated ono or more tool heads required for executing the desired tooth preparation are missing.

For example, the removal of tooth material comprises on or more of the following: a milling, a drilling.

For example, the selecting of tool heads for the tooth preparation may be executed per tooth to be prepared of the one or more teeth to be prepared. It is checked per tooth to be prepared, using the defined features of the tool heads of the plurality of tool heads, for different combinations and sequences of usage of the tool heads of the plurality of tool heads, whether the one or more preparation criteria are satisfied.

A tooth-specific selection of tool heads from the plurality of tool heads and a tooth-specific sequence of usage of the tool heads of the selection for the tooth preparation satisfying the one or more preparation criteria may be determined. The determining may comprise executing a simulation of the tooth preparation of the specific tooth to be prepared, for which the section and sequence are to be determined, using the tool heads of the selection according to the sequence of usage of the tool heads of the selection. The result of the simulation being output may further define, for which tooth to be prepared, the selection of tool heads and the sequence of usage of the tool heads of the selection are determined.

For example, the definitions of the tool heads of the plurality of tool heads define one or more of the following features of the tool heads of the plurality of tool heads: shapes of the tool heads, surface structures of the tool heads. The shapes of the tool heads refer to cutting sections configured to remove, i.e., cut away, tooth material. The cutting may, e.g., be implemented by drilling and/or milling. The surface structures of the tool heads refer to surface structures of cutting surfaces comprised by the cutting sections, which are configured to remove, i.e., cut away, tooth material.

The shape of a tool head may define a shape of a prepared tooth sections resulting from removing tooth material from a tooth to be prepared within the respective tooth section using the respective tool head. The resulting shape of the tooth sections may, e.g., be a negative of the shape of the tool head being used for removing tooth material. Depending on a shape of a target state to be achieved for a tooth to be prepared, specific shapes of tool heads may be required for achieving the respective shape of the target state to be achieved. For example, it may be required that a shape of a tool head matches a shape of at least a section of a target state to be achieved by removing tooth material form a tooth to be prepared using the respective tool head.

For example, the one or more target states defined by the three-dimensional digital target tooth model may be subtracted from the one or more current states defined by the three-dimensional digital initial tooth model. For this purpose, the three-dimensional digital target tooth model and the three-dimensional digital initial tooth model may, e.g., registered. Image registration refers to transforming different sets of data into one coordinate system. The registration may be rigid or nonrigid. The three-dimensional digital difference model resulting from the subtraction describes the tooth sections, i.e., tooth material to be removed.

For example, the shape of a tooth section being removed using a tool head may correspond to the shape of the respective tool head being used for the removal, i.e., being a positive of the respective tool head. Depending on a shape of a tooth section to be removed according the three-dimensional digital difference model, specific shapes of tool heads may be required match the shape of the respective tooth section. For example, it may be required that a shape of a tool head matches a shape of at least a part of a tooth section described by the three-dimensional digital difference model.

The surface structures of a tool head, in particular of a milling tool head, may define a surface structure of a prepared tooth sections resulting from removing tooth material from a tooth to be prepared within the respective tooth section using the respective tool head. For example, the coarser a surface structure of a tool head, the rougher or coarser the resulting surface structure of the prepared tooth sections may be. For example, the finer a surface structure of a tool head, the smoother or finer the resulting surface structure of the prepared tooth sections may be.

Furthermore, a finer surface structure of a tool head may result in a more precise tooth preparation, since inaccuracies resulting from using a tool head with a finer surface structure may be smaller compared to inaccuracies resulting from using a tool head with a coarser surface structure. A coarser surface structure of a tool head on the other side may result in a less precise tooth preparation, since inaccuracies resulting from the preparation using the tool head with a coarser surface structure may be larger compared to inaccuracies resulting from using a tool head with a coarser surface structure.

On the other hand, a tool head with a coarser surface structure may be able to remove more tooth material per time, i.e., a material removal rate may be higher, compared to a tool head with a finer surface structure. Furthermore, a shape of a tool head may set certain limits for a surface structure of the respective tool head and thus for a material removal rate achievable using this tool head.

The preparation criteria may comprise of criteria for a preparation time as well as for a precision of the preparation. In order to be able to satisfy both types of requirements, a suitable combination of tool heads may be required. For example, one or more tool heads with a comparatively coarser surface structure may be used to remove large quantities of the tooth material in a comparatively short time. For example, a shape of these tool heads with a comparatively coarser surface structure may not be a shape matching the final shape of the preparation to be achieved as defined by the three-dimensional digital target tooth model. These tool heads may be used for a basic removal of tooth material. They may be optimized regarding an amount of tooth material being removed. Then, e.g., one or more tool heads with a comparatively coarser surface structure and a shape already matching the final shape of the preparation to be achieved as defined by the three-dimensional digital target tooth model may be used. These tool heads may be used for a subsequent shaping of the sections of the teeth being prepared, after a substantial amount of tooth material has been removed. They may be optimized regarding a shaping of the sections of the teeth being prepared.

For example, a shape of the tool heads with a comparatively coarser surface structure may already be a shape matching the final shape of the preparation to be achieved as defined by the three-dimensional digital target tooth model. These tool heads may be used for a basic removal of tooth material and a shaping of the sections of the teeth being prepared at the same time.

For example, one or more tool heads with comparatively finer surface structures may be used subsequently for final surface processing and/or shaping of sections of the teeth being prepared. These tool heads may be used to achieve the final shape of the preparation to be achieved as defined by the three-dimensional digital target tooth model. For example, the final shape may be achieved successively using tool heads with shapes successively approximating the final shape to be achieved. These tool heads may be used to achieve the predefined precision of the preparation. For example, the precision may be achieved successively using tool heads with successively finer surface structures.

For example, the simulation of the tooth preparation comprises a determining of preparation trajectories for moving the tool heads of the selection according to the sequence of usage of the tool heads of the selection through the teeth to be prepared.

Thus, preparation trajectories for moving the tool heads of the selection according to the sequence of usage of the tool heads of the selection through the teeth to be prepared may be provided. These preparation trajectories may, e.g., be provided as a part of the simulation result. Thus, the simulation result may provide a guidance for moving the tool heads of the selection according to the sequence of usage of the tool heads of the selection through the teeth to be prepared. These preparation trajectories may, e.g., be provided as a reference. They may be displayed on a graphical user interface. They may even be provided using an augmented reality device such that the actual teeth to be prepared are visually overlaid with a projection of the preparation trajectories.

For example, the method further comprises executing additional different simulations of the tooth preparation with the different combinations and sequences of usage of the tool heads of the plurality of tool heads using the defined features of the respective tool heads. The different simulations are used for the checking, whether one or more preparation criteria are satisfied.

For example, a plurality of simulations of the tooth preparation may be executed. Each simulation may be executed with a different combination and/or sequence of usage of tool heads of the plurality of tool heads. For these simulations, it may be checked, whether the preparation criteria are satisfied. In case only one of the simulations satisfies the preparation criteria, the combination and sequence of usage of tool heads of this simulation may be determined as the selection of tool heads and sequence, which are provided as part of the simulation result.

In case more than one of the simulations satisfy the preparation criteria, a combination and sequence of usage of tool heads of one of this simulation may be selected as the selection of tool heads and sequence, which are provided as part of the simulation result. This selection may be executed automatically, e.g., a combination and sequence of usage of tool heads best satisfying the preparation criteria may be selected. For example, a combination and sequence of usage of tool heads may be selected, for which a resulting preparation time is minimized. For example, a combination and sequence of usage of tool heads may be selected, for which a resulting preparation precision is maximized, i.e., for which deviations from the target states defined by the three-dimensional digital target tooth model are minimized. For example, a combination and sequence of usage of tool heads may be selected, for which a combination of resulting preparation time and deviations is minimized. Thus, a combination and sequence of usage of tool heads may be selected, which enable short preparation time with a high precision.

In case more than one of the simulations satisfy the preparation criteria, the combinations and sequences of usage of tool heads of theses simulations may be output, e.g., on a graphical user interface. Then, an input may be received selecting one of these combinations and sequences of usage of tool heads as the selection of tool heads and sequence to be provided as part of the simulation result. For example, a maximum number N, e.g., 2, 3, 4, 5, 6, 7, 8, 9, or 10, of combinations and sequences of usage of tool heads of the simulations satisfying the preparation criteria are output for a final selection. For example, the top N combinations and sequences of usage of tool heads regarding the resulting preparation time and/or preparation precision are output.

The determining of the combinations and sequences of usage of tool heads may follow certain rules. For example, the tool heads may be assigned to different preparation steps. When determining simulating different combinations and sequences of usage of tool heads, tool heads may only be used for preparation steps, they are assigned to. For example, when determining combinations and sequences of usage of tool heads, it may be required, that following the sequence shapes of the tool heads are required to converge to a shape matching the final shape of the preparation to be achieved and/or surface structures of the tool heads are required become successively finer. For example, the combinations and sequences of usage of tool heads may be determined using a decision tree. When using the decision tree, e.g., only those branches may be followed for which the preparation time decreases and/or for which the resulting precision increases.

For example, the one or more preparation criteria comprise one or more first criteria for a preparation time. Using the preparation time as a preparation criterion may have the beneficial effect that a time-optimized selection and sequence of usage of the tool heads may be selected for the tooth preparation.

For example, the features of the tool heads of the plurality of tool heads are related to approximated preparation times resulting from a usage of the respective tool heads. The checking comprises a checking of the one or more first criteria using the defined features of the tool heads of the plurality of tool heads. For example, based on their surface structures and/or their surface shapes the tool heads may be assigned with tooth material removal rates. These tooth material removal rates may be used to approximate a preparation time required to remove a certain amount of tooth material using a certain tool head. For a combination of tool heads, each of the tool heads may be designated for removing a certain section of a tooth to be prepared, i.e., a certain amount of tooth material. Using the tooth material removal rates assigned to the individual tool heads, times required for the removal of the respective section may be determined. A sum of theses times may be used as an approximated preparation time for the respective combination of tool heads.

For example, the one or more first criteria define an acceptable maximum preparation time. Thus, each combination and sequence of usage of tool heads with an approximated preparation time smaller than the required maximum preparation time satisfies the respective preparation criterion.

For example, the one or more first criteria require the approximated preparation time of the determined selection and sequence to be a minimum preparation time compared to approximated preparation times of the other checked combinations and sequences of usage of the tool heads of the plurality of tool heads. Thus, only a combination and sequence of usage of tool heads with a minimum approximated preparation time satisfies the respective preparation criterion.

For example, the one or more preparation criteria comprise one or more second criteria for a precision of the tooth preparation. Using the preparation precision as a preparation criterion may have the beneficial effect that a precision-optimized selection and sequence of usage of the tool heads may be selected for the tooth preparation.

For example, three-dimensional digital target tooth model may define the precision of the tooth preparation to be achieved. For example, a definition of the precision of the tooth preparation to be achieved may be received in addition to the three-dimensional digital target tooth model. The precision of the tooth preparation may, e.g., define an allowable maximum for deviations of the simulated preparation from the target states defined by the three-dimensional digital target tooth model.

For example, the defined features of the tool heads of the plurality of tool heads are related to approximated precisions of the tooth preparation resulting from a usage of the respective tool heads. The checking comprises a checking of the one or more second criteria using the defined features of the tool heads of the plurality of tool heads.

The approximated precision may, e.g., depend on the surface structure of a tool head. For example, the finer a surface structure of a tool head, the higher an approximated precision achievable by the respective tool head. For example, the coarser a surface structure of a tool head, the lower an approximated precision achievable by the respective tool head. Thus, the tool heads may be assigned with approximated precision depending of their surface structure.

For example, the one or more second criteria define a required minimum precision. Thus, each combination and sequence of usage of tool heads with an approximated precision of the tooth preparation larger than the required minimum precision, i.e., with deviations smaller than a maximum deviation compatible with the minimum precision, satisfies the respective preparation criterion.

For example, the one or more second criteria require the approximated precision of the tooth preparation of the determined selection and sequence to be a maximum precision compared to the other checked combinations and sequences of usage of the tool heads of the plurality of tool heads. Thus, only a combination and sequence of usage of tool heads with a maximum approximated precision of the tooth preparation, i.e., with the smallest deviation, satisfies the respective preparation criterion.

For example, the definitions of the tool heads comprise three-dimensional digital tool models of the tool heads. For example, these three-dimensional digital tool models of the tool heads may be used for executing the simulations of the tooth preparation.

For example, the method further comprises generating one or more three-dimensional digital preparation guide models for one or more steps of the tooth preparation using the simulation of the tooth preparation with the tool heads of the selection according to the sequence of usage of the tool heads of the selection. The one or more three-dimensional digital preparation guide models define one or more preparation guides configured to guide a usage of one or more of the tool heads of the selection according to the respective simulation.

For example, a preparation guide may define a boundary for a preparation step. For example, a tool head may be used to remove tooth material until a resulting preparation boundary matches the boundary defined by the preparation guide. For example, a preparation guide may comprise a guiding surface or edge. For example, a tool head may be moved along the guiding surface or edge, when executing the preparation step, for which the preparation guide is configured.

The one or more preparation guides may support a dentist to properly implement the steps of the tooth preparation according to simulation using the determined selection of tool heads according to the determined sequence of usage. For example, a preparation guide may be determined and provided for each tool head of the selection of tool heads.

For example, one or more of the one or more three-dimensional preparation guides define one or more intermediate states of the tooth preparation to be achieved using the tool heads of the selection according to the sequence of usage of the tool heads of the selection.

The one or more preparation guides may support a dentist to properly implement subsequently the intermediate states of the tooth preparation by subsequently using the preparation guides. For example, an intermediate state of the tooth preparation may be defined for each tool head of the selection of tool heads. For example, a preparation guide may be determined and provided for each intermediate state of the tooth preparation and thus for each tool head of the selection of tool heads.

For example, the method further comprises providing first manufacturing data for controlling a manufacturing of one or more physical preparation guides. The first manufacturing data define the three-dimensional digital preparation guide models as templates for the physical preparation guides.

The provided first manufacturing data for controlling a manufacturing of the one or more physical preparation guides may enable a manufacturing of the respective physical preparation guides, e.g., using CAD/CAM methods.

For example, the method further comprises manufacturing of the one or more physical preparation guides using the first manufacturing data provided for controlling the manufacturing with the one or more manufactured physical preparation guides being physical copies of the templates defined by the provided first manufacturing data.

Examples may have the beneficial effect that the one or more physical preparation guides are provided for usage for executing the tooth preparation. The physical preparation guides may, e.g., be manufactured using 3D printing. The physical preparation guides may, e.g., be manufactured using machining. The physical preparation guides may, e.g., be manufactured using casting.

For example, the method further comprises a generating of the three-dimensional digital target tooth model. The generating of the three-dimensional digital target tooth model comprises determining one or more sections of the one or more teeth of the three-dimensional digital initial tooth model teeth to be removed by the tooth preparation.

For example, the generating of the three-dimensional digital target tooth model comprises identifying one or more damaged sections of the one or more teeth of the three-dimensional digital initial tooth model. For example, the determined sections to be removed comprise the one or more identified damaged sections.

For identifying damaged sections of the one or more teeth to be prepared, e.g., additional scan data of an X-ray, CT, CBCT and/or near-infrared scan may be used. The information provided by the additional scan data may, e.g., be part of the three-dimensional digital initial tooth model or may be provided in addition to the three-dimensional digital initial tooth model. For example, scan data of an X-ray and/or CBCT scan of the tooth are received. For example, DICOM data of X-ray images and/or CBCT images of the tooth are received. For example, scan data of a near-infrared scan of the tooth are received.

The additional scan data may provide insight into the teeth inner structure. A CT scan provides computer-processed combinations of multiple X-ray measurements taken from different angles to produce tomographic, i.e., cross-sectional images. For example, a focal plane tomography may be used with images of multiple planes being taken to generate a composite panoramic image. A cone-beam computed tomography (CBCT), also referred to as digital volume tomography (DVT), consisting of X-ray computed tomography with divergent X-rays forming a cone. Near-infrared (NIRI) uses electromagnetic radiation e near-infrared region of the electromagnetic spectrum to scan an internal structure, i.e., enamel and dentine, of patients' teeth. Tooth enamel is transparent to near-infrared wavelengths, while tooth dentin and other interference, e.g., caries, may show up as visual contrast. Thus, by scanning the internal structure using NIRI, interproximal caries detection may be detected.

For example, the generating of the three-dimensional digital target tooth model comprises identifying one or more unsupported tooth sections of the one or more teeth of the three-dimensional digital initial tooth model. For example, the determined sections to be removed comprise the one or more identified unsupported sections.

For example, the generating of the three-dimensional digital target tooth model comprises identifying one or more tooth sections of the one or more teeth of the three-dimensional digital initial tooth model, which have to be removed to provide sufficient space for a restoration to be arranged in and/or on the prepared tooth. For example, the determined sections to be removed comprise the one or more identified sections, which have to provide sufficient space. For example, the sufficient space may be determined using a required minimum thickness of the restoration. For example, the space provided has at least to be sufficiently large to allow for a restoration with the required minimum thickness to be arranged in and/or in the prepared tooth.

For example, the generating of the three-dimensional digital target tooth model comprises identifying one or more laterally protruding sections of the one or more teeth of the three-dimensional digital initial tooth model resulting in one or more undercuts. For example, the determined sections to be removed comprise the one or more identified laterally protruding sections.

For example, the one or more sections to be removed are determined, such that the identified sections are removed, while a resulting material loss is kept to a minimum. For example, the sections being removed are minimized.

For example, the method further comprises generating and providing control data configured for controlling a robotic device, e.g., a robotic arm, to execute the tooth preparation according to the simulation using the tool heads of the selection according to the sequence of usage of the tool heads of the selection.

Providing the control data may enable an automated execution of the tooth preparation according to the simulation using a robotic device. For example, the control data may define the selection of tool heads and the sequence of usage of these tool heads for executing the tooth preparation. Furthermore, the control data may preparation trajectories for moving the tool heads of the selection according to the sequence of usage of these tool heads through the teeth to be prepared.

For example, the method further comprises in response to a result of the checking, whether the one or more preparation criteria are satisfied, indicating that none of the checked combinations and sequences of usage of the tool heads of the plurality of tool heads satisfies the one or more preparation criteria, determining one or more additional tool heads with features configured to achieve the one or more target states satisfying the one or more preparation criteria. The plurality of tool heads is expanded by adding the one or more additional tool heads. The checking, whether the one or more preparation criteria are satisfied, is re-executed using the expanded the plurality of tool heads. The determined selection of tool heads from the plurality of tool heads comprises one or more of the one or more additional tool heads.

Example may have the beneficial effect that in case the one or more preparation criteria cannot be satisfied with the tool heads provided by the plurality of tool kits, one or more additional tool heads may be determined for meeting the one or more preparation criteria. The tool kits initially used may be tool kits available for executing a tooth preparation. However, in case the one or more preparation criteria cannot be satisfied with the tool heads available, the one or more additional tool heads may be determined and the set of available tool heads, i.e., the plurality of tool kits, may be expanded by these additional tool heads.

After the expansion, the previously unsuccessful checking may be repeated and a selection of tool heads determined, which the additional tool heads and therefore satisfies the one or more preparation criteria.

For example, the method further comprises generating one or more additional three-dimensional digital tool models of the one or more additional tool heads. Second manufacturing data for controlling a manufacturing of one or more additional physical tool heads are provided. The second manufacturing data define the additional three-dimensional digital tool models as templates for the additional physical tool heads.

The provided second manufacturing data for controlling a manufacturing of the one or more additional physical tool heads may enable a manufacturing of the respective additional physical tool heads, e.g., using CAD/CAM methods. Thus, in case the one or more preparation criteria cannot be satisfied using the tool heads available, i.e., provided by the plurality of tool kits, the available tool heads can be expanded by the additional physical tool heads. Thus, an execution of a tooth preparation satisfying the one or more preparation criteria can be enabled.

For example, the method further comprises manufacturing of the one or more additional physical tool heads using the second manufacturing data provided for controlling the manufacturing with the one or more manufactured additional physical tool heads being physical copies of the templates defined by the provided second manufacturing data.

Examples may have the beneficial effect that additional physical tool heads are provided for usage for executing the tooth preparation. Thus, a set of available tool heads may be expanded by the additional physical tool heads. The additional physical tool heads may, e.g., be manufactured using 3D printing. The additional physical tool heads may, e.g., be manufactured using machining. The additional physical tool heads may, e.g., be manufactured using casting.

The one or more teeth to be prepared may, e.g., be prepared for receiving one or more dental restoration elements. The one or more target states of the teeth to be prepared, which are described by the three-dimensional digital target tooth model may, e.g., be states prepared for receiving one or more dental restoration elements.

For example, the dental restoration element is one of the following: veneer, a coping with coating, an inlay, an onlay, an overlay, crown, a bridge, a mockup, a waxup, a provisional.

A veneer is a layer of restoration material placed over a tooth, in order to cover one or more surfaces of the tooth. Veneers may, e.g., improve the aesthetics of a smile and/or protect the tooth's surface from damage. Indirect veneers are manufactured outside of a patient's oral cavity and then arranged on a tooth within the oral cavity. Direct veneers are built-up directly on a tooth inside a patient's oral cavity. The tooth may be prepared for receiving the veneer.

For example, two main types of restoration material may be used for manufacturing a veneer: composite and dental porcelain. A composite veneer may be directly placed on the tooth, i.e., built-up in the mouth of patient, or indirectly manufactured outside the mouth of the patient and later bonded to the tooth. In contrast, a porcelain veneer may only be indirectly manufactured outside the mouth of the patient. A full veneer crown, on the one hand, is dental restoration element that is configured to cover all the coronal tooth surfaces, i.e., the mesial, distal, facial, lingual and occlusal surfaces. A laminate veneer, on the other hand, is a thin layer of restoration material that may, e.g., cover only a single surface of a tooth, e.g., a labial surface. A laminate veneer may generally be used for aesthetic purposes.

Coping with coating refers to a dental restoration element, which is directly built on the tooth to be restored. An underlying coping is arranged on the tooth. The coping is configured to replicate the performance of a natural tooth. On the coping a coating is applied, which is configured to replicate the natural aesthetics of the tooth to be restored. For example, a ceramic coating may be used. Using a coping with coating to restore a tooth may have the beneficial effect of providing a dental restoration element that combines both durability and natural aesthetics.

Inlays, onlays, and overlays are forms of indirect restoration manufactured outside of a patient's oral cavity as a single, solid piece that fits a specific size and shape of a reception prepared within a tooth of the oral cavity. The inlay, onlay, or overlay is arranged within the respective reception and bonded, e.g., cemented, in place on the prepared tooth. In contrary to a crown, inlays, onlays, and overlays are arranged within a reception prepared within a damaged tooth.

An inlay is configured to cover an inner, e.g., central, section of an occlusal surface of a tooth. Thus, an inlay may be used to replace an internal part of a damaged tooth and cover part of the occlusal surface of the respective tooth. The inlay is positioned within hard tissues of the tooth, but does not cover a cusp or pointed part of the tooth. In comparison to an inlay, an onlay in addition covers at least one of the cusps of the tooth. In comparison to an onlay, an overlay covers a larger portion of the occlusal surface of the tooth extending beyond the cusps.

The inlays, onlays, and overlays may, e.g., be configured as pinlays. Pinlays are characterized by an additional use of pins to increase their retention. Thus, any inlay, onlay, or overlay may be configured as a pinlay by being braced by pins. Such a pin may, e.g., be inserted at an edge of the tooth or parallel to a groove. In general, the base of a pin is selected to lie in a section of the tooth surface that is free of damage.

A crown is a dental restoration element in form of a dental cap. Such a crown may, e.g., be provided in form of a full coverage crown or a partial crown, like a ⅞ crown or a ¾ crown. Partial crowns, like ⅞ and ¾ crowns, are hybrids between an onlay and a full coverage crown. They are categorized based on an estimated degree of wall coverage of the walls of the prepared tooth, on which the respective crown is arranged. For example, a ¾ crown aims to cover three thirds of the walls of the tooth to be restored, e.g., three out of the four walls, e.g., with the buccal wall being spared. For example, a ⅞ crown aims to cover seven eights of the walls of the tooth to be restored. A full coverage crown completely caps or encircles a prepared tooth. A crown may, e.g., be required when a large cavity threatens the health of a tooth. A crown may be bonded to the tooth prepared for receiving the crown using a bonding material, e.g., a dental cement. A crown may be made from various materials, which may be fabricated using indirect methods, i.e., outside the patient's oral cavity. Crowns may be used to improve strength, to improve appearance of teeth and/or to halt deterioration.

A bridge is a dental restoration element in form of a permanent appliance used to replace one or more missing teeth. A dental bridge comprises a plurality of artificial dental elements that are fused together, e.g., one or more artificial replacement teeth are definitively joined to adjacent teeth. A conventional bridge may be supported, e.g., by full coverage crowns, partial crowns, overlays, onlays or inlays on the abutment teeth. The abutment teeth require preparation and reduction to support the bridge.

A mockup prosthetic restoration composite is a composite to be arranged within a patient's mouth in order to visualize for the patient a result of a prosthetic restoration, before the actual prosthetic restoration is executed. Thus, the patient as well as a dentist may assess the expected esthetic and functional outcome of the prosthetic restoration. The final result to be expected may thus be visualized at an early stage of planning prosthetic restoration. This approach may ensure that the patient as well as the dentist may the same result to be achieved in mind and allows for potential adjustments to be made prior to the final restorations manufactured and applied, e.g., cemented.

A waxup prosthetic restoration refers to a prosthetic restoration made from laboratory wax. Such a waxup prosthetic restoration is used for acquiring information indicative of whether a specific prosthetic restoration is appropriate. A planned prosthetic restoration may be generated using from laboratory wax. The waxup prosthetic restoration may be used to test, whether the planned prosthetic restoration is appropriate. Using wax may have the beneficial effect, that the waxup prosthetic restoration may be easily adjusted to also test adjustments of the planned prosthetic restoration and/or adjusting the planned prosthetic restoration to requirements determined using the waxup prosthetic restoration.

A waxup model may, e.g., be used by a doctor and/or a practitioner for visualization purposes. Furthermore, it may, e.g., also be used for generating one or more in-mouth preparation guiding surfaces, e.g., using silicon imprints, where the doctor and/or practitioner may measure and/or visually gauge, whether a planned tooth reduction has been performed.

A provisional is a type of interim dental restoration designed to be a template for the final restoration. It is used to verify, e.g., a comfort in occlusion for the patient, esthetic parameters that satisfy the patient's and dentist's expected goals and/or phonetic evaluation for speech and airflow. Esthetic parameters ma, e.g., comprise shape, midlines, smile line, embrasure shapes, and/or position of contacts. The phonetic evaluation for speech and airflow may ensure that no sibilance, whistlers, and/or lisp occur and a clear articulation being enabled by the prosthetic restoration resembled by the provisional.

Designed tooth shapes may, e.g., be re-using for manufacturing temporaries and/or final restorations. This may, e.g., be executed automatically by registering the prepared tooth after a preparation, e.g., using a re-can of the patient's detention after the preparation, with a pre-planning patient-scan, i.e., a scan of the patient's detention before the preparation and/or determination of the preparation surface. The planned three-dimensional digital dental restoration model may then, e.g., be arranged on a three-dimensional digital model of the prepared tooth generated using scan data of the prepared tooth provided by the re-can of the patient's dentition.

In another aspect a computer program product is disclosed for selecting tool heads for a tooth preparation comprising a removal of tooth material. The computer program product comprises a non-transitory computer readable storage medium having program instructions embodied therewith. The program instructions are executable by a processing unit of a computer device to cause the computer device to receive a three-dimensional digital target tooth model descriptive of one or more target states of the respective one or more teeth to be prepared. The one or more target states are to be achieved starting from the one or more current states by preparing the one or more teeth to be prepared comprising the removal of the tooth material from the respective teeth. Definitions of tool heads of a plurality of tool heads of a plurality of tool kits defining features of the tool heads of the plurality of tool heads are received.

It is checked, using the defined features of the tool heads of the plurality of tool heads, for different combinations and sequences of usage of the tool heads of the plurality of tool heads, whether one or more preparation criteria are satisfied.

A selection of tool heads from the plurality of tool heads and a sequence of usage of the tool heads of the selection for the tooth preparation satisfying the one or more preparation criteria are determined. The determining comprises executing a simulation of the tooth preparation using the tool heads of the selection according to the sequence of usage of the tool heads of the selection. The simulation is executed using the defined features of the respective tool heads of the selection. A result of the simulation is output comprising a definition of the selection of tool heads and the sequence of usage of the tool heads of the selection.

The program instructions provided by the computer program product may, e.g., be executable by the processor unit of the computer device to cause the computer device to execute any of the aforementioned examples of the method for selecting tool heads for a tooth preparation.

In another aspect a computer program is disclosed for selecting tool heads for a tooth preparation comprising a removal of tooth material. The computer program comprises instructions, which are executable by a processing unit of a computer device to cause the computer device to receive a three-dimensional digital target tooth model descriptive of one or more target states of the respective one or more teeth to be prepared. The one or more target states are to be achieved starting from the one or more current states by preparing the one or more teeth to be prepared comprising the removal of the tooth material from the respective teeth. Definitions of tool heads of a plurality of tool heads of a plurality of tool kits defining features of the tool heads of the plurality of tool heads are received.

It is checked, using the defined features of the tool heads of the plurality of tool heads, for different combinations and sequences of usage of the tool heads of the plurality of tool heads, whether one or more preparation criteria are satisfied.

A selection of tool heads from the plurality of tool heads and a sequence of usage of the tool heads of the selection for the tooth preparation satisfying the one or more preparation criteria are determined. The determining comprises executing a simulation of the tooth preparation using the tool heads of the selection according to the sequence of usage of the tool heads of the selection. The simulation is executed using the defined features of the respective tool heads of the selection. A result of the simulation is output comprising a definition of the selection of tool heads and the sequence of usage of the tool heads of the selection.

The program instructions comprised by the computer program, e.g., be executable by the processor unit of the computer device to cause the computer device to execute any of the aforementioned examples of the method for selecting tool heads for a tooth preparation.

In another aspect a computer device is disclosed for selecting tool heads for a tooth preparation comprising a removal of tooth material. The computer device comprises a processing unit and a memory storing program instructions executable by the processing unit. Execution of the program instructions by the processing unit causing the computer device to receive a three-dimensional digital target tooth model descriptive of one or more target states of the respective one or more teeth to be prepared. The one or more target states are to be achieved starting from the one or more current states by preparing the one or more teeth to be prepared comprising the removal of the tooth material from the respective teeth. Definitions of tool heads of a plurality of tool heads of a plurality of tool kits defining features of the tool heads of the plurality of tool heads are received.

It is checked, using the defined features of the tool heads of the plurality of tool heads, for different combinations and sequences of usage of the tool heads of the plurality of tool heads, whether one or more preparation criteria are satisfied.

A selection of tool heads from the plurality of tool heads and a sequence of usage of the tool heads of the selection for the tooth preparation satisfying the one or more preparation criteria are determined. The determining comprises executing a simulation of the tooth preparation using the tool heads of the selection according to the sequence of usage of the tool heads of the selection. The simulation is executed using the defined features of the respective tool heads of the selection. A result of the simulation is output comprising a definition of the selection of tool heads and the sequence of usage of the tool heads of the selection.

Execution of the program instructions by the processor of the computer device may, e.g., cause the computer device to execute any of the aforementioned examples of the method for selecting tool heads for a tooth preparation comprising a removal of tooth material.

For example, the computer device is comprised by a tool system. The tool system further comprises one or more of the tool kits of the plurality of tool kits and a robotic device. Execution of the program instructions by the processing unit further causes the computer device to generate and provide control data configured for controlling the robotic device to execute the tooth preparation according to the simulation using the tool heads of selection according to the sequence of usage of the tool heads of the selection.

For example, the tool system comprises all the tool kits of the plurality of tool kits. For example, the tool system comprises or is provided with at least the tool heads of the determined selection of tool heads. Providing at least the determined selection of tool heads as well as the control data may, e.g., enable the robotic device to be controlled to execute the tooth preparation according to the simulation of the tooth preparation using the tool heads of the selection according to the sequence of usage of the tool heads of the selection.

For example, the computer device is comprised by a manufacturing system, The manufacturing system further comprises one or more manufacturing devices configured to manufacture one or more preparation guides configured to guide a usage of the tool heads of the selection according to the simulation of the tooth preparation. Execution of the program instructions by the processing unit further causes the computer device to generate one or more three-dimensional digital preparation guide models for one or more steps of the tooth preparation using the simulation of the tooth preparation. The one or more three-dimensional digital preparation guide models define the one or more preparation guides. First manufacturing data for controlling a manufacturing of one or more physical preparation guides is provided. The first manufacturing data defines the three-dimensional digital preparation guide models as templates for the physical preparation guides.

The one or more manufacturing devices are controlled to manufacture the one or more physical preparation guides using the first manufacturing data provided for controlling the manufacturing with the manufactured physical preparation guides being physical copies of the templates defined by the first manufacturing data provided.

For the manufacturing of the one or more physical preparation guides, e.g., computer-controlled additive and/or subtractive methods may be used. For example, the one or more physical preparation guides may be manufactured using one of the following: machining, 3D printing, casting.

For example, the one or more manufacturing devices of the manufacturing system may comprise one or more of the following: a machining device, a 3D printing device.

For example, the one or more manufacturing devices of the manufacturing system further are configured for manufacturing one or more additional physical tool heads. Execution of the program instructions by the processing unit further causes the computer device to determine one or more additional tool heads with features configured to achieve the one or more target states satisfying the one or more preparation criteria. The one or more additional tool heads are determined in response to a result of the checking, whether one or more preparation criteria are satisfied, indicating that none of the checked combinations and sequences of usage of the tool heads of the plurality of tool heads satisfies the one or more preparation criteria. The plurality of tool heads is expanded by adding the one or more additional tool heads. The determined selection of tool heads from the plurality of tool heads comprises the one or more additional tool heads. One or more additional three-dimensional digital tool models of the one or more additional tool heads are generated. Second manufacturing data for controlling a manufacturing of one or more additional physical tool heads are provided. The second manufacturing data define the additional three-dimensional digital tool models as templates for the additional physical tool heads.

The one or more manufacturing devices are control to manufacture the one or more additional physical tool heads using the second manufacturing data provided for controlling the manufacturing with the manufactured additional physical tool heads being physical copies of the templates defined by the second manufacturing data provided.

For the manufacturing of the one or more additional physical tool heads, e.g., computer-controlled additive and/or subtractive methods may be used. For example, the one or more additional physical tool heads may be manufactured using one of the following: machining, 3D printing, casting.

For example, the one or more manufacturing devices of the manufacturing system may comprise one or more of the following: a machining device, a 3D printing device.

It is understood that one or more of the aforementioned examples may be combined as long as the combined examples are not mutually exclusive.

BRIEF DESCRIPTION OF THE DRAWINGS

In the following, examples are described in greater detail making reference to the drawings in which.

DETAILED DESCRIPTION

Figure 1:
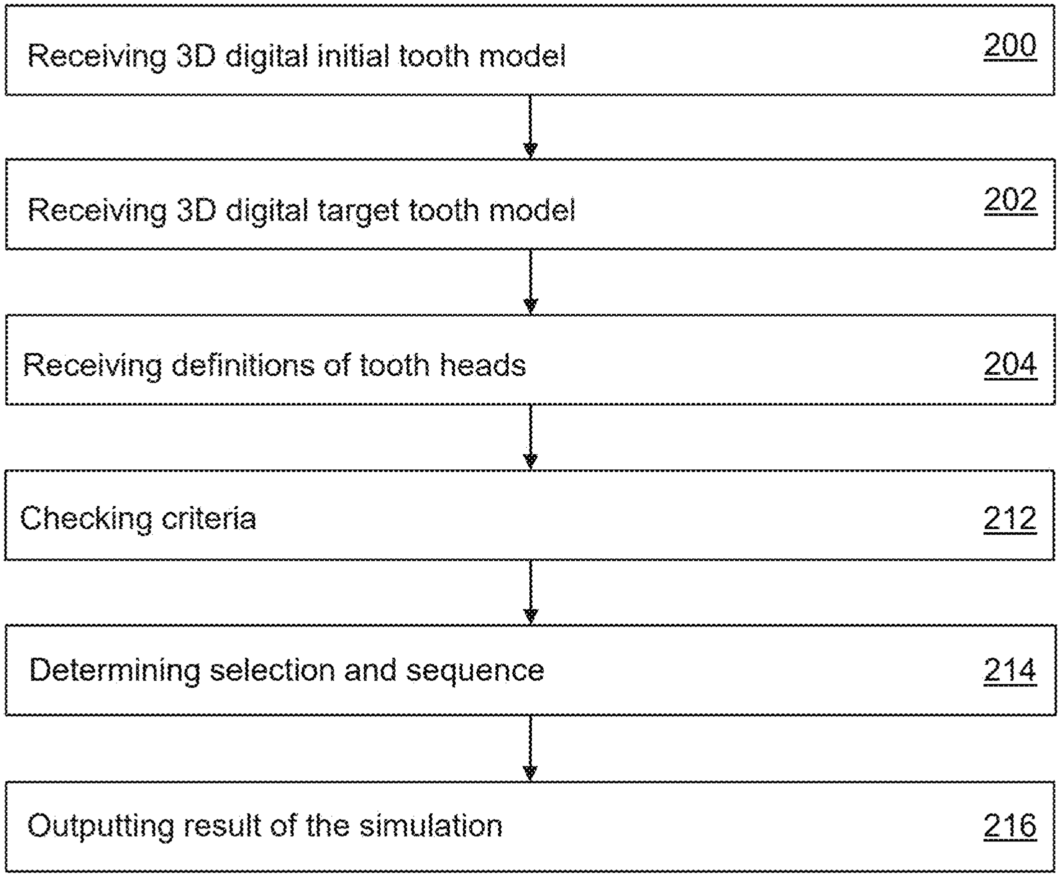
FIG. 1 is a flowchart illustrating a method for selecting tool heads for a tooth preparation.

In the following, similar elements are denoted by the same reference numerals.

FIG. 1 shows an exemplary computer-implemented method for selecting tool heads for a tooth preparation comprising a removal of tooth material. In block 200, a three-dimensional digital initial tooth model descriptive of one or more current states of one or more teeth to be prepared is received. In block 202, a three-dimensional digital target tooth model descriptive of one or more target states of the respective one or more teeth to be prepared is received. The one or more target states are to be achieved starting from the one or more current states by preparing the one or more teeth to be prepared comprising the removal of the tooth material from the respective teeth. The tooth material may, e.g., be removed using milling and/or drilling. For example, the received the three-dimensional digital target tooth model is a predefined model. For example, the predefined three-dimensional digital target tooth model has been predefined using the three-dimensional digital initial tooth model. For example, the three-dimensional digital initial tooth model and the three-dimensional digital target tooth model are received together.

The three-dimensional digital initial tooth model may, e.g., comprise scan data of the teeth. The scan data of the teeth may comprise, e.g., optical scan data. The optical scan data may, e.g., comprise intraoral optical scan data of the teeth or optical scan data from an optical scan of a classical mold/impression of the teeth. The optical scan data may, e.g., provide information about a surface structure of the teeth. The scan data may, e.g., provide information about sub-surface structures of the teeth. The scan data of the teeth may, e.g., comprise near-infrared scan data. The scan data of the teeth may, e.g., comprise scan data acquired using a medical imaging technique, like computed tomography (CT), cone beam computed tomography (CBCT), and/or digital volume tomography (DVT).

The three-dimensional digital initial tooth model may, e.g., be a model of the one or more teeth to be prepared only. The three-dimensional digital initial tooth model may, e.g., be provided in form of a dentition model of a dentition comprising the respective one or more teeth to be prepared.

The three-dimensional digital target tooth model may, e.g., be a model of the one or more prepared teeth only. The three-dimensional digital initial tooth model may, e.g., be provided in form of a dentition model of a dentition comprising the respective one or more prepared teeth.

For example, the receiving of the three-dimensional digital target tooth model in block 202 comprises a generating of the three-dimensional digital target tooth model being received. The generating of the three-dimensional digital target tooth model may, e.g., comprise identifying one or more damaged sections of the one or more teeth of the three-dimensional digital initial tooth model and determining one or more sections of the respective teeth to be removed by the tooth preparation. The determined sections to be removed comprise the one or more identified damaged sections. For example, the one or more sections to be removed are determined, such that the identified damaged sections are removed, while a resulting material loss is kept to a minimum. Alternatively, a predefined three-dimensional digital target tooth model. For example, the three-dimensional digital initial tooth model and the three-dimensional digital target tooth model are received separately.

In block 204, definitions of tool heads of a plurality of tool heads of a plurality of tool kits defining features of the tool heads of the plurality of tool heads are received. The tool heads may, e.g., comprise milling tool heads and/or drilling tool heads. For example, the definitions of the tool heads of the plurality of tool heads may define shapes of the tool heads. For example, the definitions of the tool heads of the plurality of tool heads may define surface structures of the tool heads. For example, the definitions of the tool heads comprise three-dimensional digital tool models of the tool heads.

In block 212, it is checked, using the defined features of the tool heads of the plurality of tool heads, for different combinations and sequences of usage of the tool heads of the plurality of tool heads, whether one or more preparation criteria are satisfied.

For example, the one or more preparation criteria comprise one or more first criteria for a preparation time. For example, the features of the tool heads of the plurality of tool heads are related to approximated preparation times resulting from a usage of the respective tool heads. The checking comprises a checking of the one or more first criteria using the defined features of the tool heads of the plurality of tool heads. For example, the one or more first criteria define an acceptable maximum preparation time. For example, the one or more first criteria require the approximated preparation time of the determined selection and sequence to be a minimum preparation time compared to approximated preparation times of the other checked combinations and sequences of usage of the tool heads of the plurality of tool heads.

For example, the one or more preparation criteria comprise one or more second criteria for a precision of the tooth preparation. For example, the defined features of the tool heads of the plurality of tool heads are related to approximated precisions of the tooth preparation resulting from a usage of the respective tool heads. The checking comprises a checking of the one or more second criteria using the defined features of the tool heads of the plurality of tool heads. For example, the one or more second criteria define a required minimum precision. For example, the one or more second criteria require the approximated preparation time of the determined selection and sequence to be a maximum precision compared to the other checked combinations and sequences of usage of the tool heads of the plurality of tool heads.

For example, different simulations of the tooth preparation using the different combinations and sequences of usage of the tool heads of the plurality of tool heads are executed. For the different simulations of the tooth preparation the defined features of the respective tool heads are used. The different simulations are used for the checking in block 212, whether one or more preparation criteria are satisfied.

In block 214, a selection of tool heads from the plurality of tool heads and a sequence of usage of the tool heads of the selection for the tooth preparation satisfying the one or more preparation criteria are determined. The determining comprises executing a simulation of the tooth preparation using the tool heads of the selection according to the sequence of usage of the tool heads of the selection. The simulation is executed using the defined features of the respective tool heads of the selection. For example, the simulation of the tooth preparation comprises a determining of preparation trajectories for moving the tool heads of the selection according to the sequence of usage of the tool heads of the selection through the teeth to be prepared.

In block 216, a result of the simulation is output comprising a definition of the selection of tool heads and the sequence of usage of the tool heads of the selection.

Figure 2:
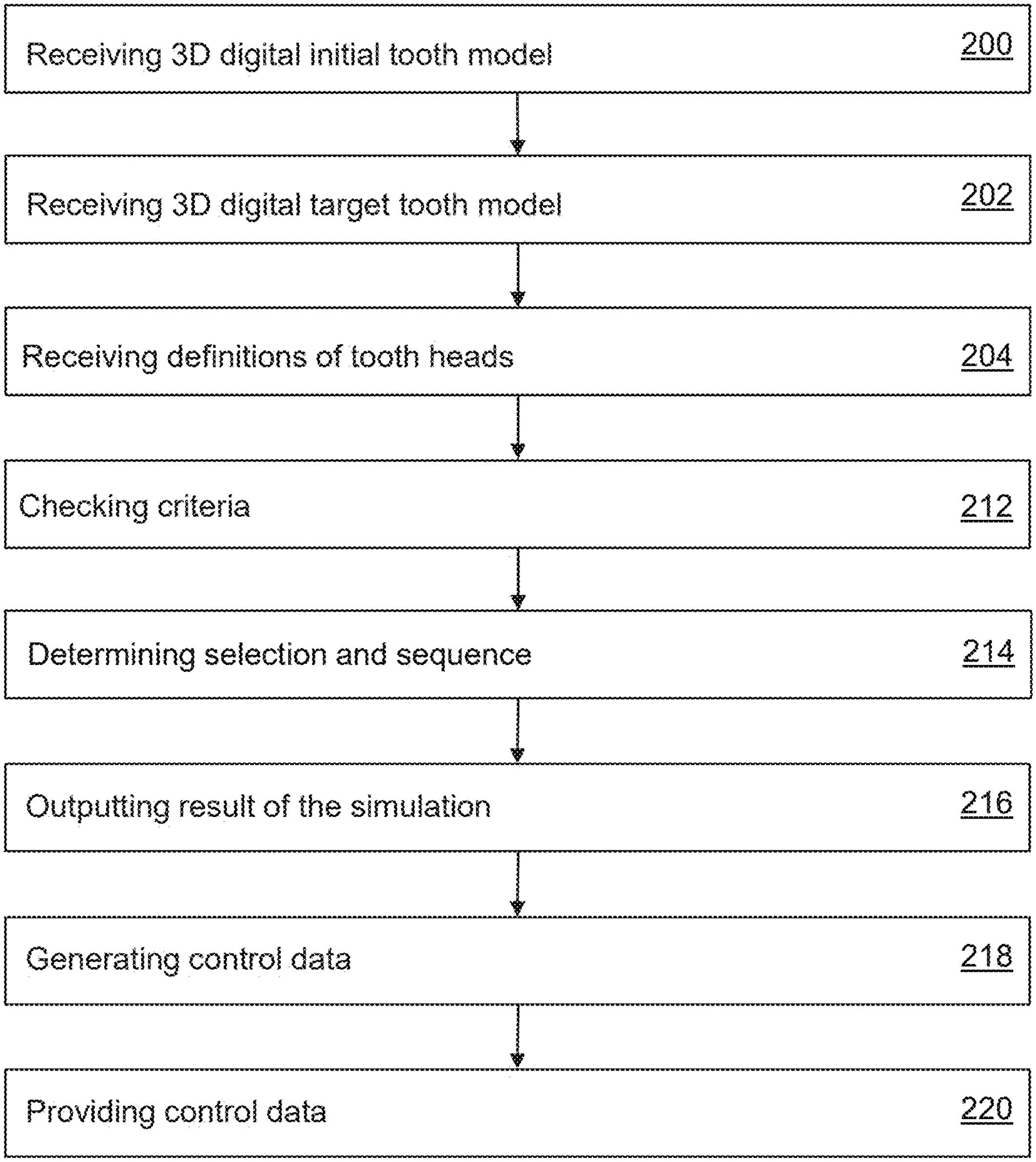
FIG. 2 is a flowchart illustrating a method for selecting tool heads for a tooth preparation and providing control data.

FIG. 2 shows another exemplary computer-implemented method for selecting tool heads for a tooth preparation comprising a removal of tooth material as well as for providing control data configured for controlling a robotic device. Blocks 200 to 204 of FIG. 2, e.g., correspond to bocks 200 to 204 of FIG. 1. Blocks 212 to 216 of FIG. 2, e.g., correspond to bocks 212 to 216 of FIG. 1.

In block 218, control data configured for controlling a robotic device, e.g., a robotic arm, to execute the tooth preparation according to the simulation is generated. The control data is configured to controlling the robotic device to execute the preparation using the tool heads of the selection according to the sequence of usage of the tool heads of the selection. In block 220, the generated control data is provided for controlling the robotic device. The control data may, e.g., be stored in a computer device configured as a control device for controlling the robotic device. The control data may be provided, e.g., on a server to be downloaded by the computer device configured as a control device for controlling the robotic device.

Figure 3:
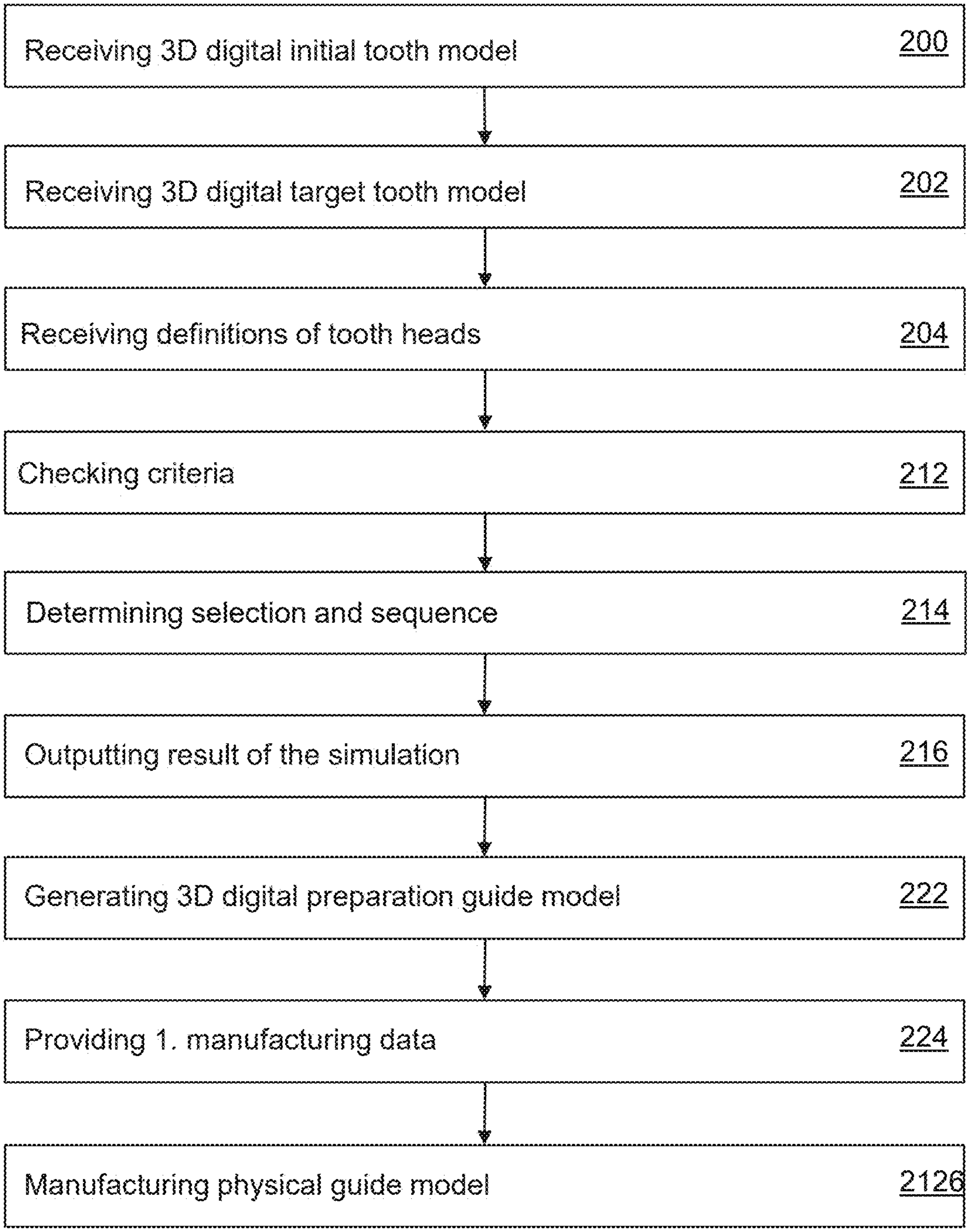
FIG. 3 is a flowchart illustrating a method for selecting tool heads for a tooth preparation and manufacturing physical guide models.

FIG. 3 shows an exemplary computer-implemented method for selecting tool heads for a tooth preparation comprising a removal of tooth material as well as for manufacturing one or more physical guide models. Blocks 200 to 204 of FIG. 3, e.g., correspond to bocks 200 to 204 of FIG. 1. Blocks 212 to 216 of FIG. 3, e.g., correspond to bocks 212 to 216 of FIG. 1.

In block 222, one or more three-dimensional digital preparation guide models for one or more steps of the tooth preparation are generated using the simulation of the tooth preparation using the tool heads of the selection according to the sequence of usage of the tool heads of the selection. For example, each step of the tooth preparation is executed by one of the tool heads of the selection. For example, the steps follow the sequence of usage determined for the tool heads of the selection. The one or more three-dimensional digital preparation guide models define one or more preparation guides configured to guide a usage of one or more of the tool heads of the selection according to the respective simulation. For example, one or more of the one or more three-dimensional preparation guides define one or more intermediate states of the tooth preparation to be achieved using the different tool heads of the selection.

In block 224, first manufacturing data for controlling a manufacturing of one or more physical preparation guides is provided, e.g., generated. The first manufacturing data define the three-dimensional digital preparation guide models as templates for the physical preparation guides. In block 226, the one or more physical preparation guides are manufactured using the first manufacturing data provided for controlling the manufacturing with the one or more manufactured physical preparation guides. The manufactured physical preparation guides are physical copies of the templates defined by the provided first data.

Figure 4:
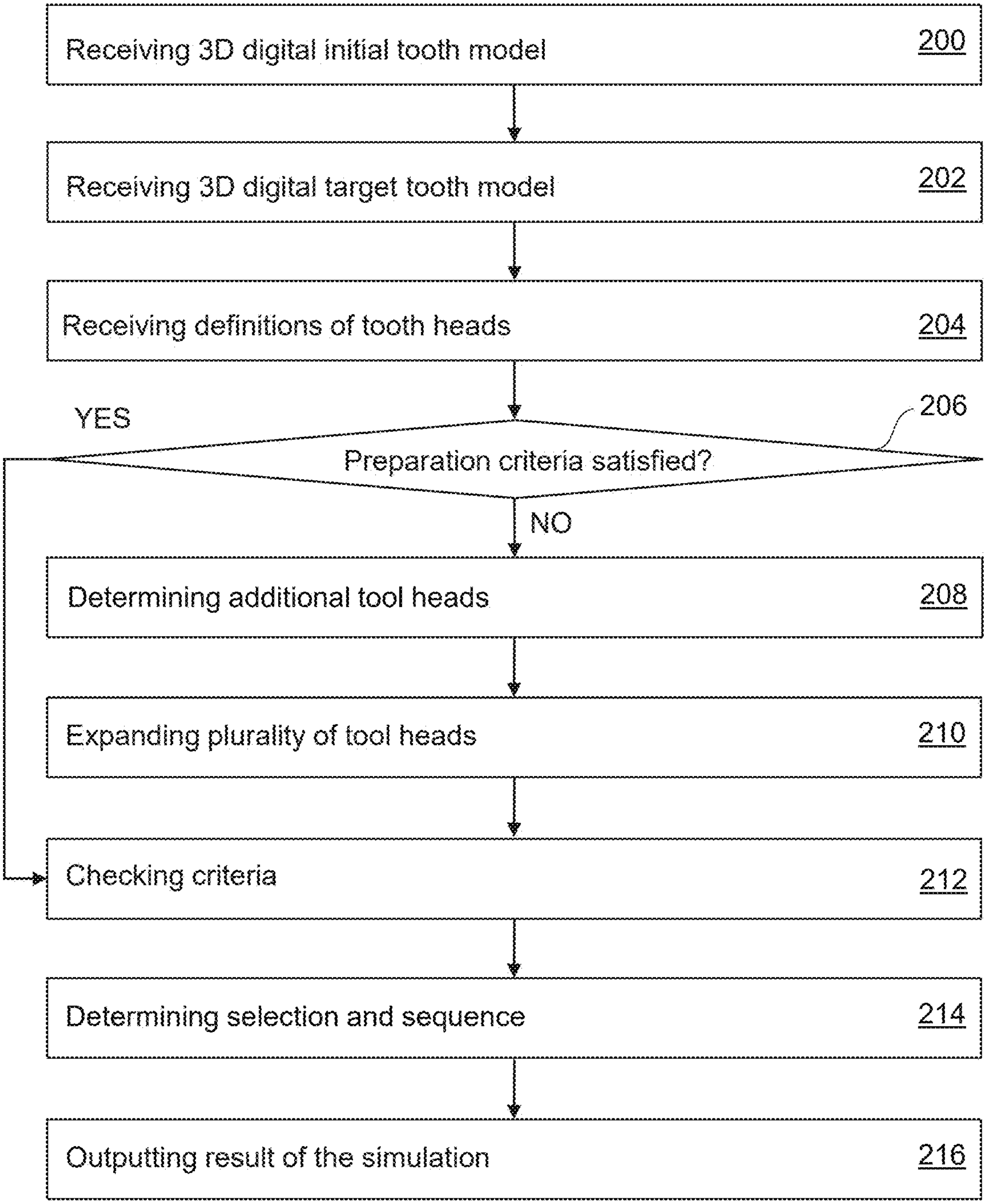
FIG. 4 is a flowchart illustrating a method for selecting tool heads for a tooth preparation and determining additional tool heads.

FIG. 4 shows an exemplary computer-implemented method for selecting tool heads for a tooth preparation comprising a removal of tooth material as well as determining additional tool heads. Blocks 200 to 204 of FIG. 4, e.g., correspond to bocks 200 to 204 of FIG. 1.

In block 206, it is checked, using the defined features of the tool heads of the plurality of tool heads, the one or more preparation criteria can be satisfied using a combination of tool heads of the plurality of tool heads.

For example, the one or more preparation criteria comprise one or more first criteria for a preparation time. For example, the features of the tool heads of the plurality of tool heads are related to approximated preparation times resulting from a usage of the respective tool heads. The checking comprises a checking of the one or more first criteria using the defined features of the tool heads of the plurality of tool heads. For example, the one or more first criteria define an acceptable maximum preparation time. For example, the one or more first criteria require the approximated preparation time of the determined selection and sequence to be a minimum preparation time compared to approximated preparation times of the other checked combinations and sequences of usage of the tool heads of the plurality of tool heads.

For example, the one or more preparation criteria comprise one or more second criteria for a precision of the tooth preparation. For example, the defined features of the tool heads of the plurality of tool heads are related to approximated precisions of the tooth preparation resulting from a usage of the respective tool heads. The checking comprises a checking of the one or more second criteria using the defined features of the tool heads of the plurality of tool heads. For example, the one or more second criteria define a required minimum precision. For example, the one or more second criteria require the approximated preparation time of the determined selection and sequence to be a maximum precision compared to the other checked combinations and sequences of usage of the tool heads of the plurality of tool heads.

In response to a result of the checking, which indicates that none of the checked combinations and sequences of usage of the tool heads of the plurality of tool heads can satisfies the one or more preparation criteria, one or more additional tool heads with features configured to achieve the one or more target states satisfying the one or more preparation criteria are determined in block 208. In block 210, the plurality of tool heads is expanded by adding the one or more additional tool heads. In block 212, the checking, whether the one or more preparation criteria are satisfied, is re-executed using the expanded the plurality of tool heads. In block 214, a selection of tool heads from the plurality of tool heads and a sequence of usage of the tool heads of the selection for the tooth preparation satisfying the one or more preparation criteria are determined. The determined selection of tool heads from the plurality of tool heads comprises one or more of the one or more additional tool heads. For example, the determining comprises executing a simulation of the tooth preparation using the tool heads of the selection according to the sequence of usage of the tool heads of the selection. The simulation is executed using the defined features of the respective tool heads. For example, the simulation of the tooth preparation comprises a determining of preparation trajectories for moving the tool heads of the selection according to the sequence of usage of the tool heads of the selection through the teeth to be prepared.

In block 216, a result of the simulation is output comprising a definition of the determined selection of tool heads and the determined sequence of usage of the tool heads of the selection. Blocks 212 to 216 of FIG. 4, e.g., correspond to bocks 212 to 216 of FIG. 1.

Figure 5A:
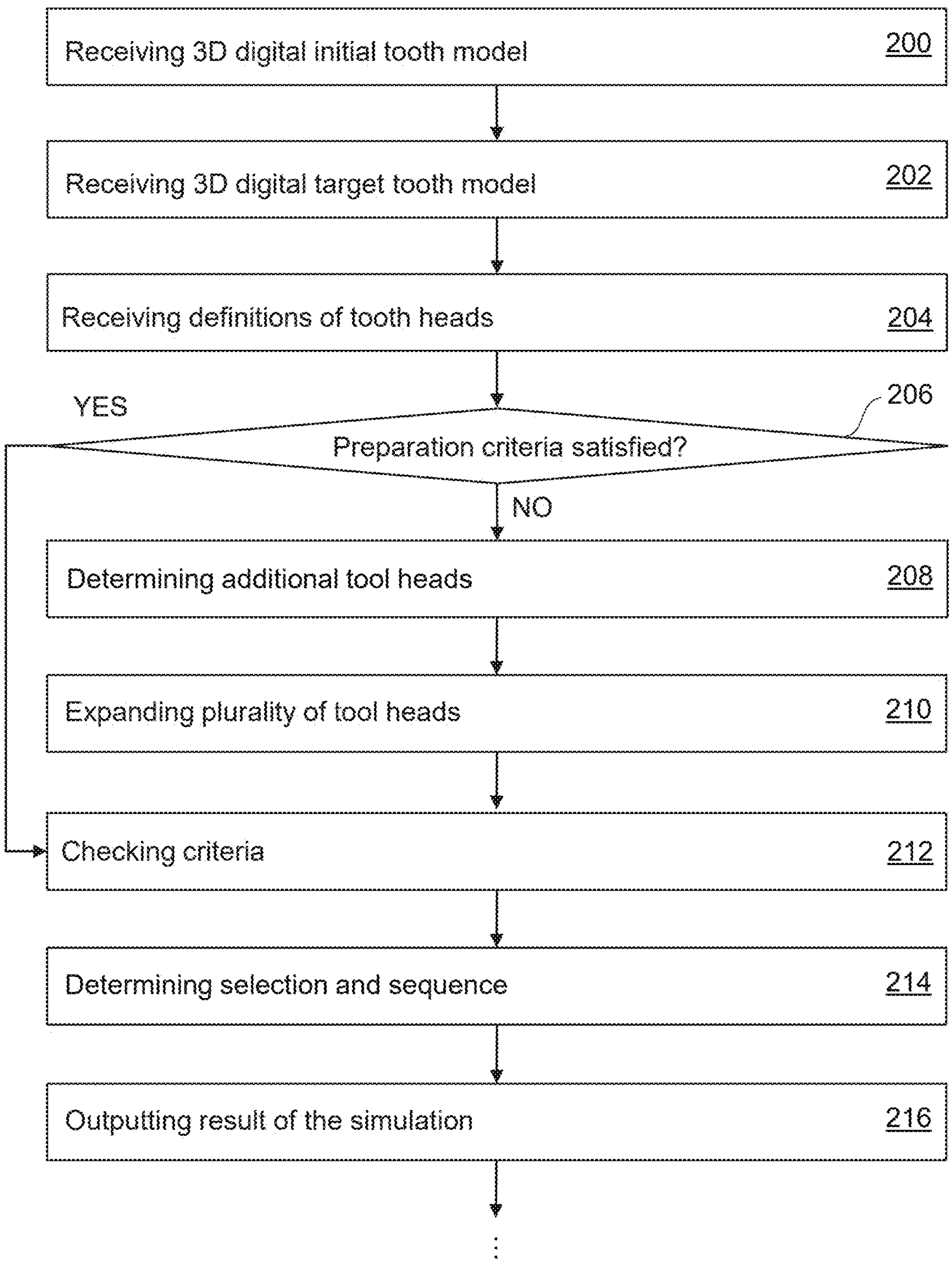
FIG. 5A is a first part of a flowchart illustrating a method for selecting tool heads for a tooth preparation and manufacturing additional tool heads.

FIG. 5A shows a first part of an exemplary computer-implemented method for selecting tool heads for a tooth preparation comprising a removal of tooth material and manufacturing additional tool heads. This exemplary computer-implemented method for selecting tool heads for a tooth preparation comprising a removal of tooth material and manufacturing additional tool heads is described by the combination FIGS. 5A and 5B. Blocks 200 to 204 of FIG. 5A, e.g., correspond to bocks 200 to 204 of FIG. 1.

In block 206, it is checked, using the defined features of the tool heads of the plurality of tool heads, the one or more preparation criteria can be satisfied using a combination of tool heads of the plurality of tool heads.

For example, the one or more preparation criteria comprise one or more first criteria for a preparation time. For example, the features of the tool heads of the plurality of tool heads are related to approximated preparation times resulting from a usage of the respective tool heads. The checking comprises a checking of the one or more first criteria using the defined features of the tool heads of the plurality of tool heads. For example, the one or more first criteria define an acceptable maximum preparation time. For example, the one or more first criteria require the approximated preparation time of the determined selection and sequence to be a minimum preparation time compared to approximated preparation times of the other checked combinations and sequences of usage of the tool heads of the plurality of tool heads.

For example, the one or more preparation criteria comprise one or more second criteria for a precision of the tooth preparation. For example, the defined features of the tool heads of the plurality of tool heads are related to approximated precisions of the tooth preparation resulting from a usage of the respective tool heads. The checking comprises a checking of the one or more second criteria using the defined features of the tool heads of the plurality of tool heads. For example, the one or more second criteria define a required minimum precision. For example, the one or more second criteria require the approximated preparation time of the determined selection and sequence to be a maximum precision compared to the other checked combinations and sequences of usage of the tool heads of the plurality of tool heads.

In response to a result of the checking, which indicates that none of the checked combinations and sequences of usage of the tool heads of the plurality of tool heads can satisfies the one or more preparation criteria, one or more additional tool heads with features configured to achieve the one or more target states satisfying the one or more preparation criteria are determined in block 208. In block 210, the plurality of tool heads is expanded by adding the one or more additional tool heads. In block 212, the checking, whether the one or more preparation criteria are satisfied, is re-executed using the expanded the plurality of tool heads. In block 214, a selection of tool heads from the plurality of tool heads and a sequence of usage of the tool heads of the selection for the tooth preparation satisfying the one or more preparation criteria are determined. The determined selection of tool heads from the plurality of tool heads comprises one or more of the one or more additional tool heads. For example, the determining comprises executing a simulation of the tooth preparation using the tool heads of the selection according to the sequence of usage of the tool heads of the selection. The simulation is executed using the defined features of the respective tool heads of the selection. For example, the simulation of the tooth preparation comprises a determining of preparation trajectories for moving the tool heads of the selection according to the sequence of the selection usage of the tool heads of the selection through the teeth to be prepared.

In block 216, a result of the simulation is output comprising a definition of the determined selection of tool heads and the determined sequence of usage of the tool heads of the selection. Blocks 212 to 216 of FIG. 5A, e.g., correspond to bocks 212 to 216 of FIG. 1.

Figure 5B:
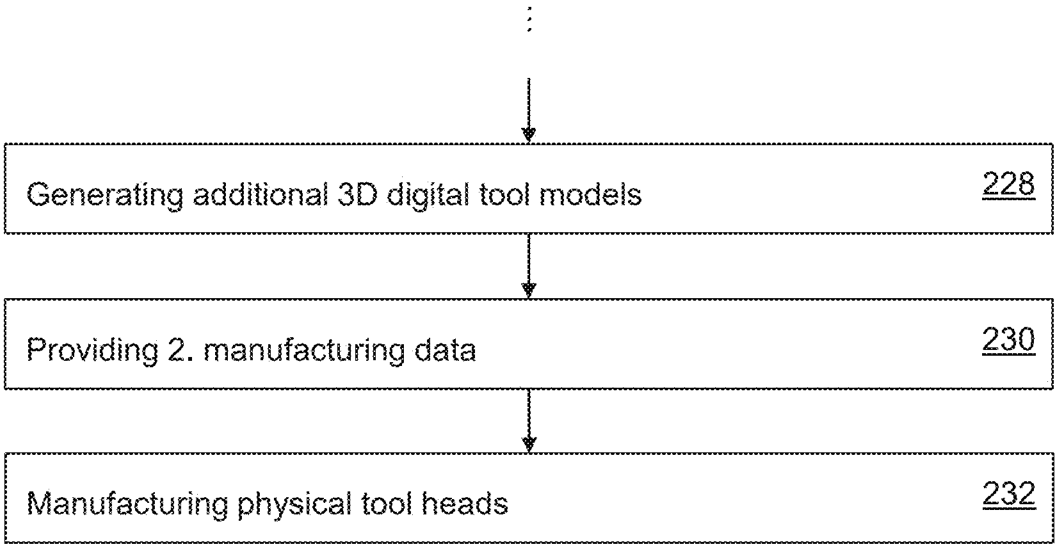
FIG. 5B is a second part of a flowchart illustrating a method for selecting tool heads for a tooth preparation and manufacturing additional tool heads.

FIG. 5B shows a second part of the exemplary computer-implemented method for selecting tool heads for a tooth preparation comprising a removal of tooth material and manufacturing additional tool heads. FIG. 5B continues the method of FIG. 5A. This exemplary computer-implemented method for selecting tool heads for a tooth preparation comprising a removal of tooth material and manufacturing additional tool heads is described by the combination FIGS. 5A and 5B.

In block 228, one or more additional three-dimensional digital tool models of the one or more additional tool heads are generated. In block 230, second manufacturing data for controlling a manufacturing of one or more additional physical tool heads are provided. The second data define the additional three-dimensional digital tool models as templates for the additional physical tool heads. In block 232, the one or more additional physical tool heads are manufactured using the second data provided for controlling the manufacturing. The one or more manufactured additional physical tool heads are physical copies of the templates defined by the provided second data.

Figure 6:
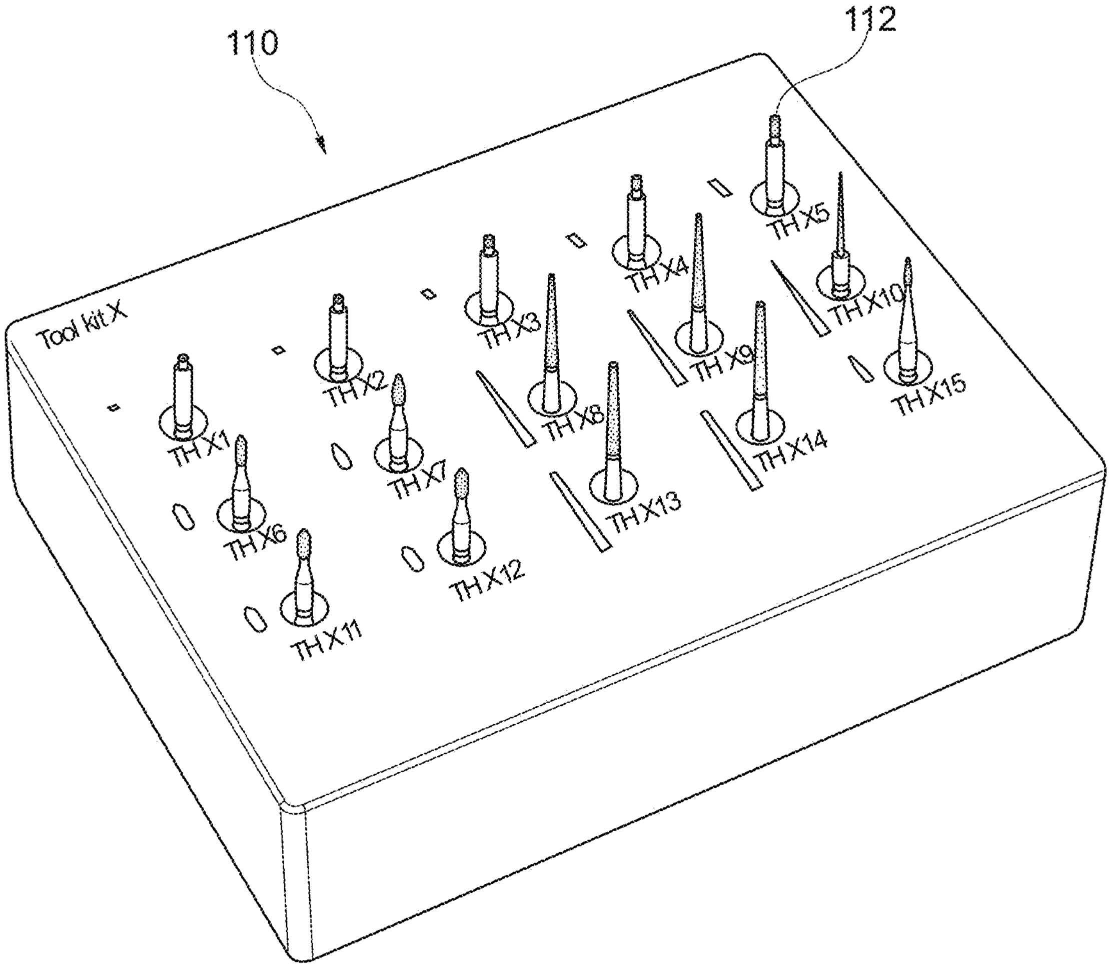
FIG. 6 shows an exemplary tool kit comprising a plurality of exemplary tool heads.

FIG. 6 shows an exemplary tool kit 110 comprising a plurality of tool heads 112. These tool heads 112 are milling tool heads and configured for usage for a tooth preparation. Each tool head 112 may be different and may be configured for executing a specific step of the tooth preparation. The tool heads 112 may, e.g., differ in terms of shape and/or surface structure. Examples may have the beneficial effect that a selection of tool heads from a plurality of tool kits and a sequence of usage of these selected tool heads may be determined, which are enable a tooth preparation satisfying one or more predefined preparation criteria. Thus, even in case it is not possible to meet the preparation criteria with the tool heads 112 provided by tool kit 110, by selecting and combining tool heads from different tool kits, like tool kit 110, it may still be possible to meet the preparation criteria. In case it is possible to meet the tool heads 112 provided by tool kit 110, the selection may comprise a combination of the tool heads 112 provided by the tool kit 110. Thus, a user can be sure that a tooth preparation satisfying the preparation criteria can be executed using the tool heads 112 of tool kit 110. In addition, the user will be informed by the simulation result, which tool heads 112 of tool kit 110 to use according to which sequence.

Figure 7:
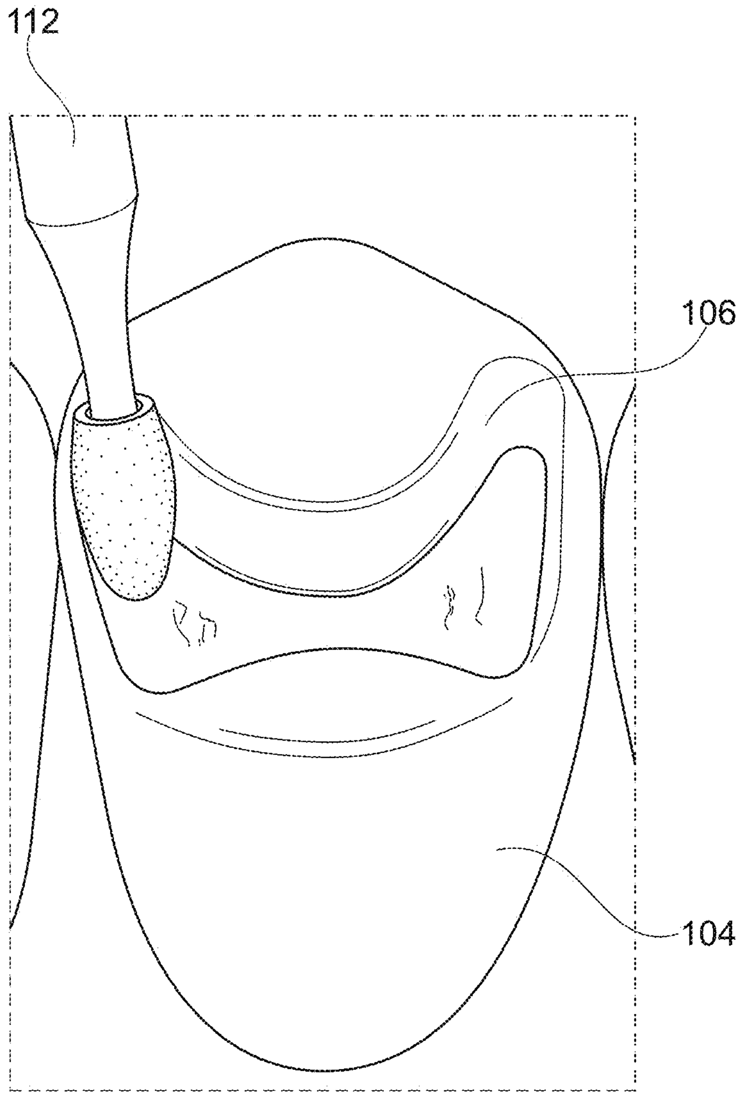
FIG. 7 shows an exemplary preparation of a tooth.
Figure 8:
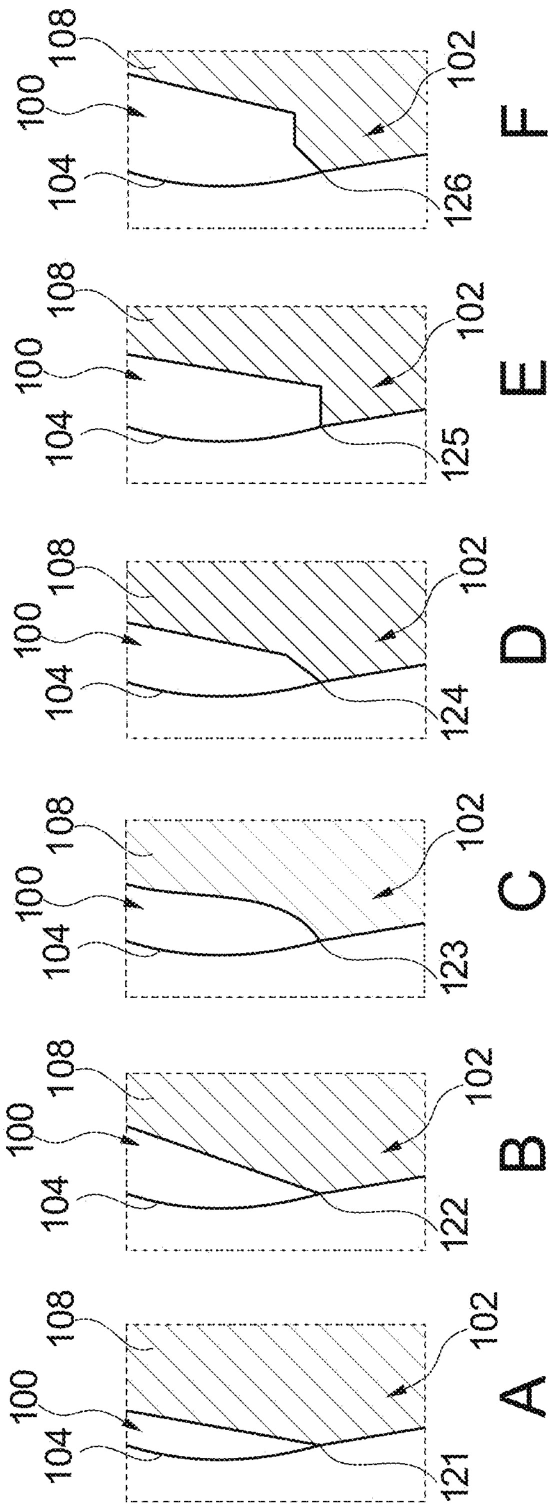
FIG. 8 shows exemplary preparations edges.

FIG. 7 shows an exemplary tooth preparation of a tooth 104 using a tool head 112. The tooth preparation comprises a removal of tooth material. The resulting shape of the prepared section 106 of tooth 104 may depend on a shape of tool head 112. For example, the resulting shape of the prepared section 106 of tooth 104 may be a negative of the shape of tool head 112. Furthermore, a tooth material removal rate and thus a preparation time required for executing the tooth preparation may depend on a surface structure of tool head 112. For example, the coarser the surface structure of tool head 112, the higher the tooth material removal rate may be. For example, a tooth material removal rate may also depend on the shape of the tool head 112. The larger a section of contact between the tool head 112 and the prepared section 106 of tooth 104 is, the higher the tooth material removal rate may be. The size of the section of contact between the tool head 112 and the prepared section 106 of tooth 104 may, e.g., corelate with a size of the tool head 112. Here, the size of the tool head 112 is considered to be part of the definition of the shape of the tool head 112.

For example, a precision of the tooth preparation may depend on the surface structure of tool head 112. For example, the coarser the surface structure of tool head 112, the lower a resulting precision may be. Furthermore, the precision of the tooth preparation may also depend on the shape of the tool head 112. The more precisely the shape of the tool head 112 meets a target shape of the tooth preparation, i.e., the more precisely the shape of the tool head 112 corresponds as a negative to the shape of the of the tooth preparation to be achieved as a positive, the higher the precision of the preparation may be.

FIG. 7 shows different exemplary types of preparation edges, stepless edges as well as edges comprising a step. In order to be able to implement these different types of preparation edges, tool heads with different shapes may be required. The more precisely a shape of a tool head corresponds as a negative to the shape of preparation edge to be achieved as a positive, the higher the precision of the preparation may be. FIG. 7 comprises six schematic illustrations A to F of exemplary preparation edges. Illustration A shows an exemplary preparation of a tooth 104 resulting in a prepared tooth 108 comprising a feather edge 121. The feather edge 121 is a stepless edge. Illustration B shows an exemplary preparation of a tooth 104 resulting in a prepared tooth 108 comprising a knife edge 122. The knifer edge 122 may as well be considered a stepless edge. All the other edges 123 to 126 of FIG. 7 are not stepless, but rather result in a detectable step. Illustration C shows an exemplary preparation of a tooth 104 resulting in a prepared tooth 108 comprising a chamfer edge 123. Illustration D shows an exemplary preparation of a tooth 104 resulting in a prepared tooth 108 comprising a bevel edge 124. Illustration E shows an exemplary preparation of a tooth 104 resulting in a prepared tooth 108 comprising a shoulder edge 125. Illustration F shows an exemplary preparation of a tooth 104 resulting in a prepared tooth 108 comprising a beveled shoulder edge 126. The tooth 104 in FIG. 7 may show a current state of tooth 104, which is described by a three-dimensional digital initial tooth model 100. The prepared tooth 108 in FIG. 7 may show a target state of tooth 104, which is described by a three-dimensional digital target tooth model 102.

Figure 9:
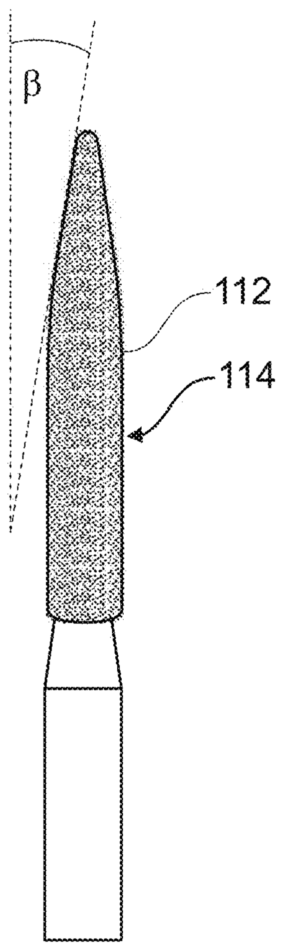
FIG. 9 shows an exemplary tool head.

FIG. 9 shows an exemplary tapered tool head 112. A tapering of the tapered tool head 112 is defined by a taper angle β. Using the tapered tool head 112 for preparing a section of a tooth to be prepared may result in a section tapered in a coronal direction. A preparation angle of the prepared section, in case of a tapered section a taper angle, may depend on the taper angle β of the tapered tool head 112. Furthermore, a tooth material removal rate and thus a preparation time may depend on a surface structure of a cutting surface 114 of the tool head 112. Also, a precision of a preparation may depend on the surface structure of the cutting surface 114 of the tool head 112

Figure 10:
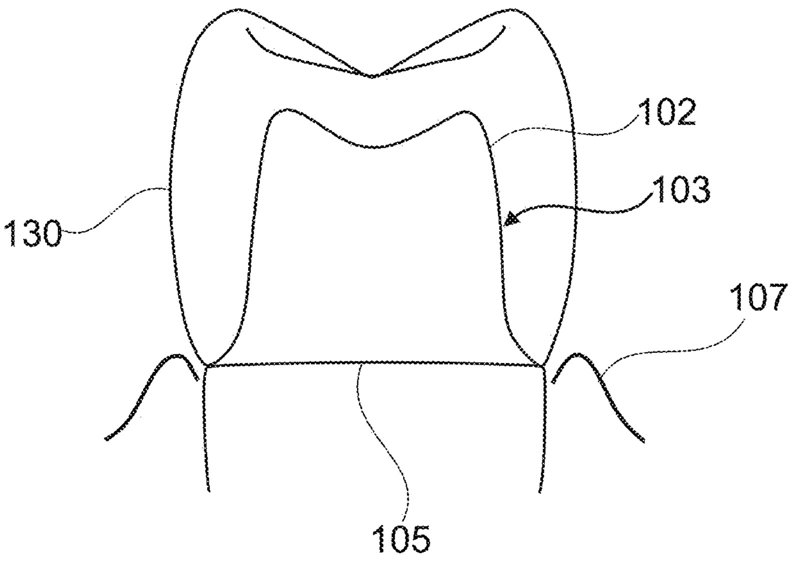
FIG. 10 shows an exemplary preparation of a tooth.

FIG. 10 shows a cross-sectional view of an exemplary three-dimensional digital dental restoration model 130 defining a dental restoration element to be arranged on a prepared molar tooth. In the example of FIG. 10, the restoration is a crown. The prepared tooth may be prepared as defined by a three-dimensional digital target tooth model 102. The three-dimensional digital dental restoration model 130 may be configured to be arranged on a preparation section 103 of the prepared tooth as defined by the three-dimensional digital target tooth model 102. The three-dimensional digital target tooth model 102 may, e.g., be provided in form of a three-dimensional digital dentition model, which in addition comprises a three-dimensional digital gingiva model 107 descriptive of a form and a position of a gingiva around the prepared tooth described by the three-dimensional digital target tooth model 102 within the dentition. A boundary 105 of the preparation section 103, e.g., in form of a cervical margin line, also referred to as finish line, may, e.g., be of one of the following types: feather edge, knife edge, chamfer, bevel, shoulder, beveled shoulder.

Figure 11:
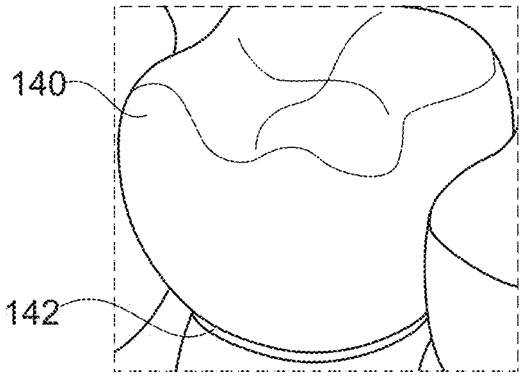
FIG. 11 shows an exemplary restoration element.

FIG. 11 shows an exemplary dental restoration element 140, e.g., as described by the three-dimensional digital dental restoration model 130 of FIG. 10, in form of a crown for a molar tooth arranged on a prepared molar tooth 142. The prepared molar tooth 142 may, e.g., be prepared as defined by the three-dimensional digital target tooth model 102 of FIG. 10.

Figure 12:
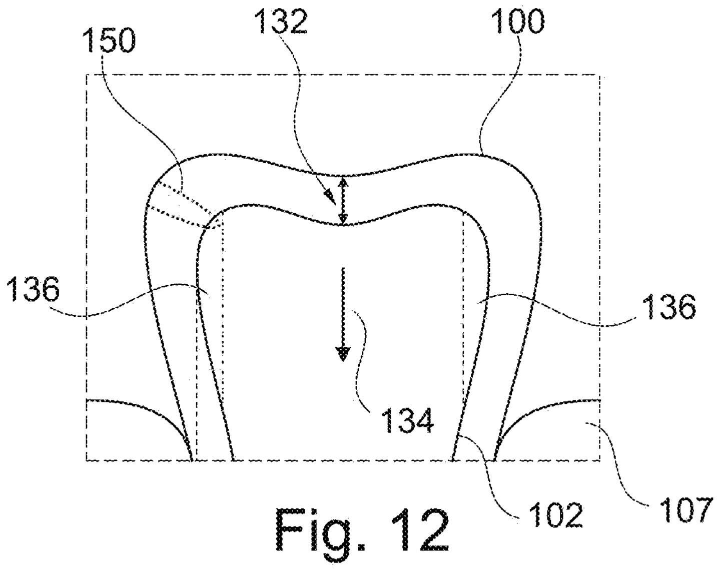
FIG. 12 shows an exemplary three-dimensional digital target tooth model.

FIG. 12 shows a cross-sectional view of an exemplary three-dimensional digital initial tooth model 100 and a three-dimensional digital target tooth model 102. The three-dimensional digital initial tooth model 100 may, e.g., be reduced by a predefined volume having a thickness comprising a required minimum material thickness 132 required by a predefined restoration material of a dental restoration element to be arranged on the prepared tooth. The thickness may further comprise a predefined additional minimum space for applying a bonding material for bonding the dental restoration element.

A preparation, i.e., the three-dimensional digital target tooth model 102 may further be adjusted to block out in an insertion direction 134 of the dental restoration element undercuts 138 remaining after the volume reduction. For this purpose, preparation parameters, i.e., the three-dimensional digital target tooth model 102, may be determined such that sections 136 may be removed by the preparation as well. The insertion direction 134 may, e.g., extend perpendicular to an occlusal plane.

Alternatively or additionally, the tooth to be prepared may comprise one or more defects 150, i.e., damaged sections, to be repaired by the preparation and restoration to be applied to the respective tooth. The preparation parameters, i.e., the three-dimensional digital target tooth model 102, may further be adjusted to also remove any section 136 of the three-dimensional digital initial tooth model 100, which comprises at least a part of the defect 150, thereby completely removing the defects 150.

Figure 13:
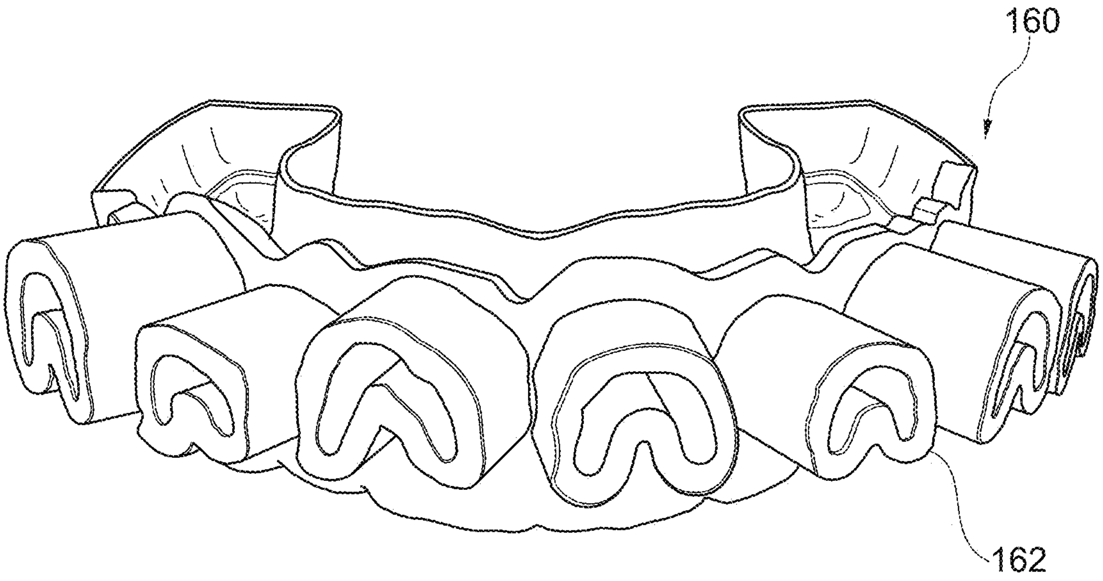
FIG. 13 shows an exemplary three-dimensional digital preparation guide model.

FIG. 13 shows an exemplary preparation guide 160. The preparation guide 160 may have a splint-like form and be configured to be arranged on a set of teeth to be prepared. The preparation guide 160 may comprise guiding elements 162. These guiding elements 162 may, e.g., in the preparation guide 160. They may, e.g., have the form of a preparation trajectory determined for a tool head of the selection of tool heads using a simulation. Additionally or alternatively, the guiding elements 162 may define boundaries of a preparation step to be executed using the respective tool head. When arranging the preparation guide 160 on a set of teeth to be prepared and inserting the tool head into the guiding elements 162, a tooth preparation using the respective tool head may easily be implemented by following the guiding elements 162 and thus the preparation trajectory determined for the tool head. In addition, the guiding elements 162 of the preparation guide 160 may comprise stops, limiting an insertion depth of the tool head into the guiding elements 162. Thus, a preparation depth may also be limited by the preparation guide 160.

Figure 14:
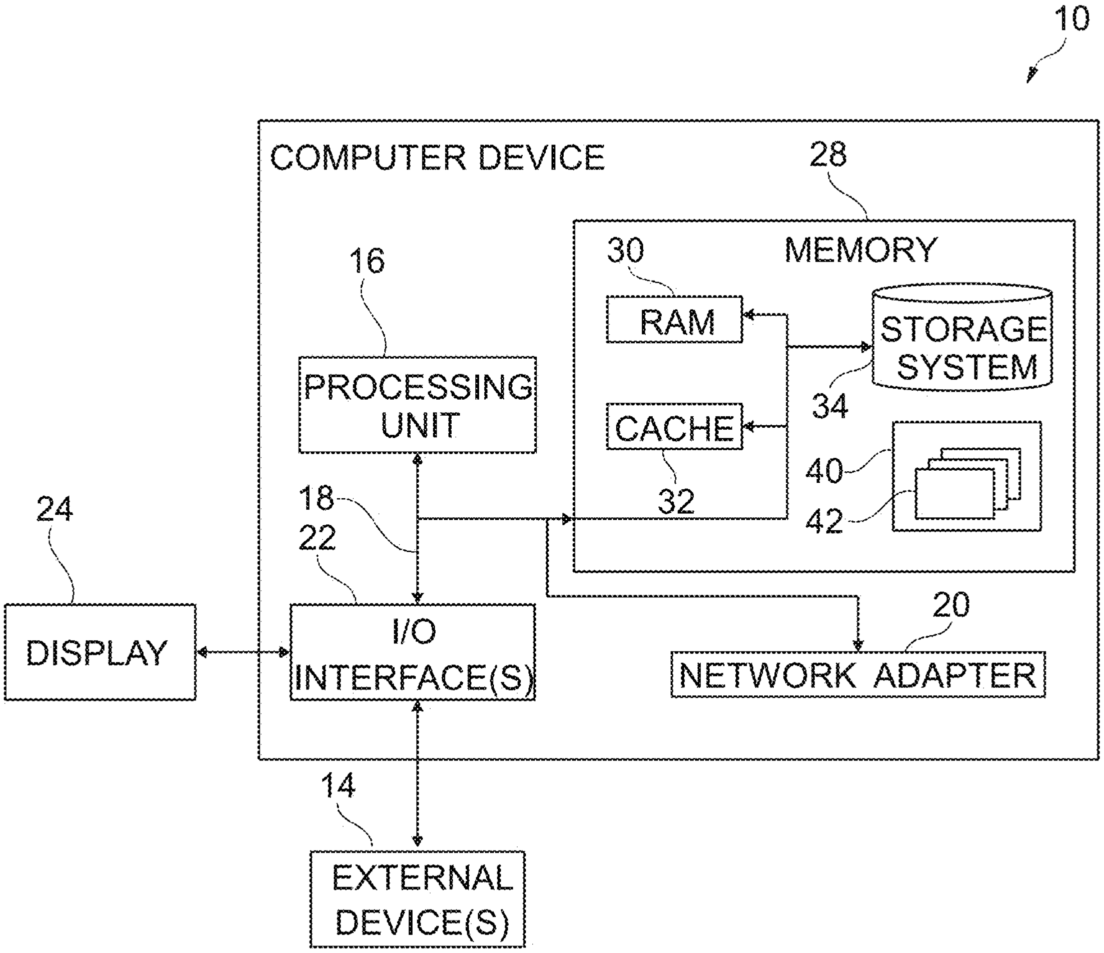
FIG. 14 shows an exemplary computer device for selecting tool heads.

FIG. 14 shows a schematic diagram of an exemplary computer device 10 for selecting tool heads for a tooth preparation comprising a removal of tooth material. The computer device 10 may be operational with numerous other general-purpose or special-purpose computing system environments or configurations. Computer device 10 may be described in the general context of computer device executable instructions, such as program modules comprising executable program instructions, being executable by the computer device 10. Generally, program modules may include routines, programs, objects, components, logic, data structures, and so on that perform particular tasks or implement particular abstract data types. Computer device 10 may be practiced in distributed computing environments where tasks are performed by remote processing devices that are linked through a communications network. In a distributed computing environment, program modules may be located in both local and remote computer device storage media including memory storage devices.

In FIG. 14, computer device 10 is shown in the form of an exemplary general-purpose computing device. The components of computer device 10 may include, but are not limited to, one or more processors or processing units 16, a system memory 28, and a bus 18 that couples various system components including system memory 28 to processor 16. Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer device 10 may comprise a variety of computer device readable storage media. Such media may be any available storage media accessible by computer device 10, and include both volatile and non-volatile storage media, removable and non-removable storage media.

A system memory 28 may include computer device readable storage media in the form of volatile memory, such as random-access memory (RAM) 30 and/or cache memory 32. Computer device 10 may further include other removable/non-removable, volatile/non-volatile computer device storage media. For example, storage system 34 may be provided for reading from and writing to a non-removable, non-volatile magnetic media also referred to as a hard drive. For example, a magnetic disk drive for reading from and writing to a removable, non-volatile magnetic disk, e.g., a floppy disk, and an optical disk drive for reading from or writing to a removable, non-volatile optical disk such as a CD-ROM, DVD-ROM or other optical storage media may be provided. In such instances, each storage medium may be connected to bus 18 by one or more data media interfaces. Memory 28 may, e.g., include a three-dimensional digital initial tooth model descriptive of one or more current states of one or more teeth to be prepared.

The three-dimensional digital initial tooth model may, e.g., comprise scan data of the teeth. The scan data of the teeth may comprise, e.g., optical scan data. The optical scan data may, e.g., comprise intraoral optical scan data of the teeth or optical scan data from an optical scan of a classical mold/impression of the teeth. The optical scan data may, e.g., provide information about a surface structure of the teeth. The scan data may, e.g., provide information about sub-surface structures of the teeth. The scan data of the teeth may, e.g., comprise near-infrared scan data. The scan data of the teeth may, e.g., comprise scan data acquired using a medical imaging technique, like computed tomography (CT), cone beam computed tomography (CBCT), and/or digital volume tomography (DVT).

Memory 28 may, e.g., include a three-dimensional digital target tooth model. The three-dimensional digital target tooth model descriptive of one or more target states of the respective one or more teeth to be prepared is received. The one or more target states are to be achieved starting from the one or more current states of the teeth as defined by the three-dimensional digital initial tooth model by preparing the one or more teeth to be prepared. The preparing comprises the removal of the tooth material from the respective teeth.

Memory 28 may, e.g., include definitions of tool heads of a plurality of tool heads of a plurality of tool kits. The definitions define features of the tool heads of the plurality of tool heads. For example, the definitions may identify tool heads available for usage. These tool heads may comprise different types of tool heads provided by different tool kits. The definitions may identify the individual tool heads, the tol kits they are part of and/or structural features of the tool heads. The structural features may, e.g., define shapes and/or surface structures of the tool heads.

Memory 28 may, e.g., include definitions of one or more preparation criteria for checking different combinations and sequences of usage of the tool heads. The one or more preparation criteria may, e.g., comprise one or more criteria for a preparation time. The one or more preparation criteria may, e.g., comprise one or more criteria for precision of the tooth preparation.

Memory 28 may, e.g., include a result of a simulation of the tooth preparation. The simulated tooth preparation may be a tooth preparation using a selection of tool heads from the plurality of tool heads and a sequence of usage of the tool heads of the selection for the tooth preparation satisfying the one or more preparation criteria. The result of the simulation may comprise a definition of the determined selection of tool heads and the determined sequence of usage of the tool heads of the selection. The simulation may comprise a determining of preparation trajectories for moving the tool heads of the selection according to the sequence of usage of the tool heads of the selection through the teeth to be prepared. The result of the simulation further may comprise definitions of the respective preparation trajectories.

Memory 28 may, e.g., include one or more three-dimensional digital preparation guide models for one or more steps of the tooth preparation using the simulation of the tooth preparation with the tool heads of the selection according to the sequence of usage of the tool heads of the selection. The one or more three-dimensional digital preparation guide models define one or more preparation guides configured to guide a usage of one or more of the tool heads of the selection according to the simulation. One or more of the one or more three-dimensional preparation guides define one or more intermediate states of the tooth preparation to be achieved using the different tool heads of the selection. Memory 28 may, e.g., include first manufacturing data for controlling a manufacturing of the one or more physical preparation guides. The first manufacturing data defines the three-dimensional digital preparation guide models as templates for the physical preparation guides.

Memory 28 may, e.g., include definitions of one or more additional tool heads with features configured to achieve the one or more target states satisfying the one or more preparation criteria. Memory 28 may, e.g., include one or more additional three-dimensional digital tool models of the one or more additional tool heads. The memory 28 may, e.g., include second manufacturing data for controlling a manufacturing of one or more additional physical tool heads. The second manufacturing data define the additional three-dimensional digital tool models as templates for the additional physical tool heads.

Memory 28 may, e.g. include control data configured for controlling a robotic device to execute the tooth preparation according to the simulation using simulation using the tool heads of selection according to the sequence of usage of the tool heads of the selection.

Program 40 may have a set of one or more program modules 42 and by way of example be stored in memory 28. The program modules 42 may comprise an operating system, one or more application programs, other program modules, and/or program data. Each of these program modules 42, i.e., the operating system, the one or more application programs, the other program modules, and/or the program data or some combination thereof, may include an implementation of a networking environment. One or more of the program modules 42 may be configured for executing a method for selecting tool heads for a tooth preparation comprising a removal of tooth material.

One or more of the program modules 42 may be configured for controlling one or more manufacturing devices to manufacture one or more physical preparation guides. One or more of the program modules 42 may be configured for controlling one or more manufacturing devices to manufacture one or more additional physical tool heads.

One or more of the program modules 42 may, e.g., be configured for executing one or more of the methods of FIGS. 1 to 5.

Computer device 10 may further communicate with one or more external devices 14 such as a keyboard, a pointing device, like a mouse, and a display 24 enabling a user to interact with computer device 10. Such communication can occur via input/output (I/O) interfaces 22. Computer device 10 may further communicate with one or more networks such as a local area network (LAN), a general wide area network (WAN), and/or a public network, like the Internet, via network adapter 20. Network adapter 20 may communicate with other components of computer device 10 via bus 18. It should be understood that although not shown, other hardware and/or software components could be used in conjunction with computer device 10.

The computer device 10 shown in FIG. 14 may be configured for selecting tool heads for a tooth preparation comprising a removal of tooth material. The method for selecting tool heads executed by computer device 10 may, e.g., comprise receiving a three-dimensional digital initial tooth model descriptive of one or more current states of one or more teeth to be prepared. A three-dimensional digital target tooth model descriptive of one or more target states of the respective one or more teeth to be prepared is received. The one or more target states are to be achieved starting from the one or more current states by preparing the one or more teeth to be prepared comprising the removal of the tooth material from the respective teeth. Definitions of tool heads of a plurality of tool heads of a plurality of tool kits defining features of the tool heads of the plurality of tool heads are received.

It is checked, using the defined features of the tool heads of the plurality of tool heads, for different combinations and sequences of usage of the tool heads of the plurality of tool heads, whether one or more preparation criteria are satisfied. A selection of tool heads from the plurality of tool heads and a sequence of usage of the tool heads of the selection for the tooth preparation satisfying the one or more preparation criteria are determined. The determining comprises executing a simulation of the tooth preparation using the tool heads of the selection according to the sequence of usage of the tool heads of the selection. The simulation is executed using the defined features of the respective tool heads of the selection. A result of the simulation is output comprising a definition of the selection of tool heads and the sequence of usage of the tool heads of the selection.

The computer device 10 shown in FIG. 14 may, e.g., further be configured for providing first manufacturing data for controlling a manufacturing of one or more physical preparation guides. The first manufacturing data define the three-dimensional digital preparation guide models as templates for the physical preparation guides. In addition, the computer device 10 may, e.g., be configured for controlling the manufacturing of one or more physical preparation guides with the one or more manufactured physical preparation guides being physical copies of the templates defined by the provided first manufacturing data.

The computer device 10 shown in FIG. 14 may, e.g., further be configured for generating and providing control data configured for controlling a robotic device, e.g., a robotic arm, to execute the tooth preparation according to the simulation using the tool heads of the selection according to the sequence of usage of the tool heads of the selection.

The computer device 10 shown in FIG. 14 may, e.g., further be configured for providing second manufacturing data for controlling a manufacturing of one or more additional physical tool heads are provided. The second manufacturing data may define additional three-dimensional digital tool models as templates for the additional physical tool heads. In addition, the computer device 10 may, e.g., be configured for controlling the manufacturing of the one or more additional physical tool heads with the one or more manufactured physical tool heads being physical copies of the templates defined by the provided second manufacturing data.

Figure 15:
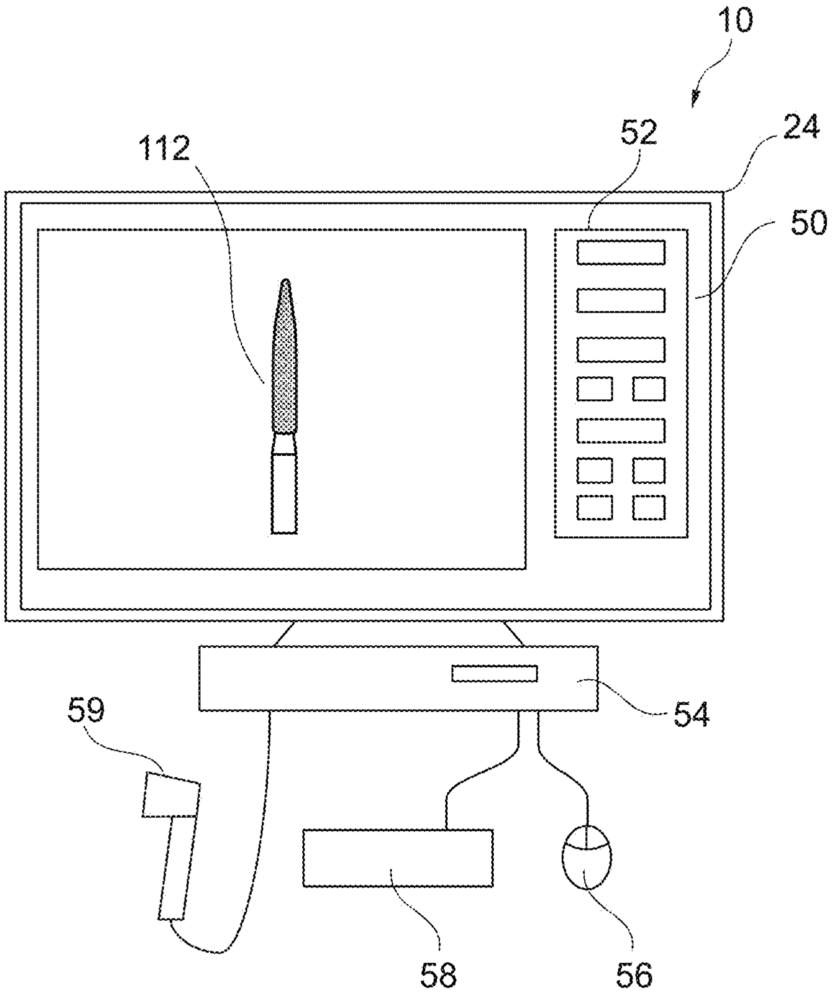
FIG. 15 shows an exemplary computer device for selecting tool heads.

FIG. 15 shows an exemplary computer device 10 for selecting tool heads 112 for a tooth preparation comprising a removal of tooth material. The computer device 10 may, e.g., be configured as shown in FIG. 14. The computer device 10 may comprise a hardware component 54 comprising one or more processing units as well as a memory storing machine-executable program instructions. Execution of the program instructions by the one or more processors may cause the one or more processors to control the computer device 10 to, e.g., select tool heads 112 for a tooth preparation comprising a removal of tooth material. The computer device 10 may check, using defined features of tool heads 112 of a plurality of tool heads 112, for different combinations and sequences of usage of the tool heads 112 of the plurality of tool heads 112, whether one or more preparation criteria are satisfied. The computer device 10 may determine a selection of tool heads 112 from the plurality of tool heads 112 and a sequence of usage of the tool heads 112 of the selection for the tooth preparation satisfying the one or more preparation criteria. The determining may comprise executing a simulation of the tooth preparation using the tool heads 112 of the selection according to the sequence of usage of the tool heads 112 of the selection. The simulation may be executed using the defined features of the respective tool heads 112 of the selection. A result of the simulation may be output comprising a definition of the selection of tool heads 112 and the sequence of usage of the tool heads 112 of the selection.

The computer device 10 may further comprise one or more input devices, like a keyboard 58 and a mouse 56, enabling a user to interact with the computer device 10. Furthermore, the computer device 10 may comprise one or more output devices, like a display 24 providing a graphical user interface 50 with control elements 52, e.g., GUI elements, enabling the user to control the selecting tool heads 112 for a tooth preparation. The computer device 10 may further comprise an exemplary scanner 59 configured for scanning a patient's mouth. The scanner 59 may, e.g., comprise an optical scanner configured for scanning, e.g., a patient's oral cavity, an imprint of a patient's oral cavity and/or a positive of a patient's oral cavity generated using an imprint. The scanner 59 may, e.g., comprise a near-infrared scanner. The scanner 59 may, e.g., comprise an CT or CBCT scanning system.

Figure 16:
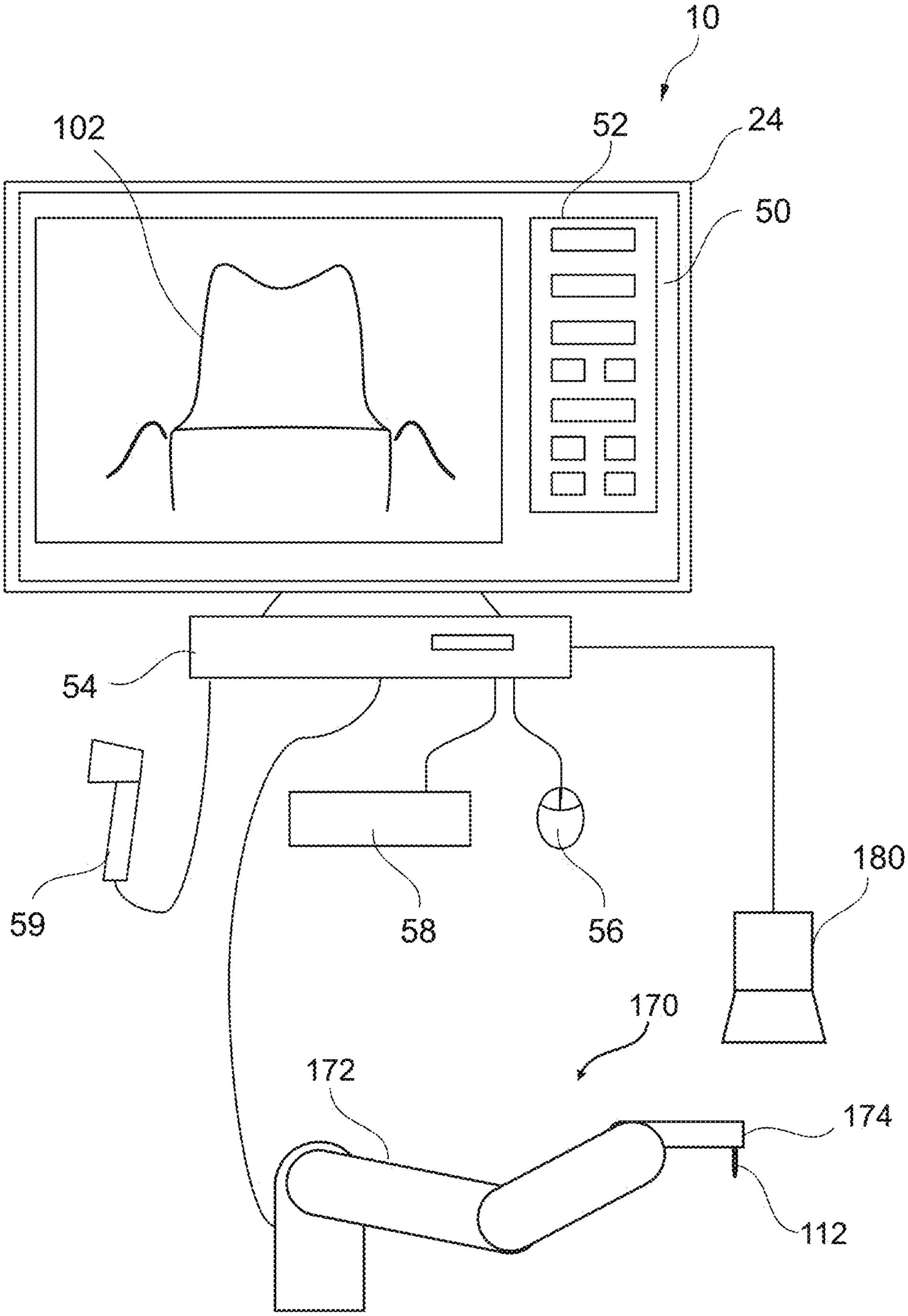
FIG. 16 shows an exemplary computer device for providing control data configured to control a robotic device.

FIG. 16 shows an exemplary computer device 10 for selecting tool heads 112 for a tooth preparation comprising a removal of tooth material. The computer device 10 may, e.g., be configured as shown in FIG. 14 and/or FIG. 15. The computer device 10 may further be configured for generating and providing control data configured for controlling a robotic device 170, e.g., comprising a robotic arm 172, to execute the tooth preparation according to the simulation using the tool heads 112 of the selection according to the sequence of usage of the tool heads of the selection. Using the provided control data, a preparation may be executable, which results in a set of one or more teeth prepared as defined by the three-dimensional digital target tooth model 102. The robotic device 172 may be configured to move a mechanical preparation instrument 174 used to perform a dental preparation procedure, including a removal of tooth material using a tool head 112 inserted into the preparation instrument. The preparation instrument 174 may, e.g., comprise internal mechanical components that initiate a rotational force and provide power to the tool head 112 for removing tooth material. Furthermore, an optical sensor 180 may be used for enabling a monitoring of a progression of the tooth preparation.

Figure 17:
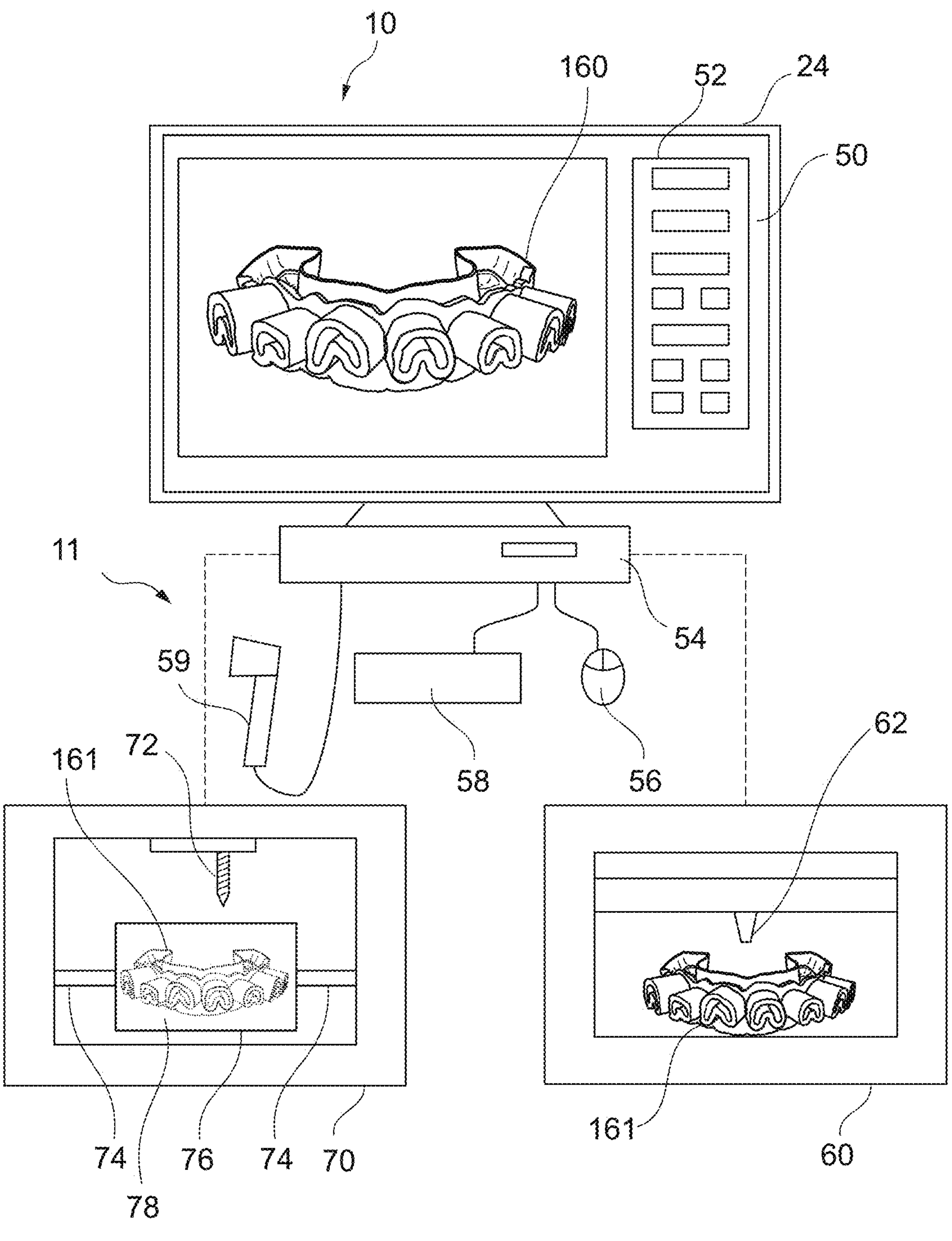
FIG. 17 shows an exemplary system for manufacturing physical guide models and/or additional tool heads.

FIG. 17 shows an exemplary manufacturing system 11. The manufacturing system 11 may, e.g., be configured for manufacturing one or more physical preparation guides 161. The one or more physical preparation guides 161 may be configured to guide a usage of one or more of the tool heads of the selection according to a simulation of a tooth preparation. The tooth preparation is a tooth preparation using tool heads of a determined selection of tool heads and according to a determined sequence of usage of the tool heads of the selection.

For manufacturing the one or more physical preparation guides 161, first manufacturing data provided for controlling the manufacturing may be used. The first manufacturing data may define one or more three-dimensional digital preparation guide models 160 as templates for the physical preparation guides 161. The one or more manufactured physical preparation guides 161 may be physical copies of the templates defined by the provided first manufacturing data.

The manufacturing system 11 may, e.g., be configured for manufacturing one or more additional physical tool heads. The one or more additional tool heads may have features configured to achieve one or more target states of one or more teeth to be prepared satisfying one or more reparation criteria.

For manufacturing the one or more physical additional physical tool heads, second manufacturing data provided for controlling the manufacturing may be used. The second manufacturing data may define one or more additional three-dimensional digital tool models as templates for the additional physical tool heads. The one or more manufactured physical tool heads being physical copies of the templates defined by the provided second manufacturing data.

The manufacturing system 11 may comprise the computer device 10 of FIG. 15. The computer device 10 may further be configured to control one or more manufacturing devices 60, 70. For controlling the one or more manufacturing devices 60, 70 a processing unit of the computer device 10 may execute program instructions. Execution of the program instructions by the processing unit may cause the computer device 10 to control the one or more manufacturing devices 60, 70 to manufacture one or more elements to be used for the preparation.

The one or more elements to be used for the preparation may, e.g., comprise the one or more physical preparation guides 161. Execution of the program instructions by the processing unit may cause the computer device 10 to control the one or more manufacturing devices 60, 70 to manufacture the one or more physical preparation guides 161 using the first manufacturing data provided for controlling the manufacturing of the physical preparation guides 161.

The one or more elements to be used for the preparation may, e.g., comprise the one or more physical additional physical tool heads. Execution of the program instructions by the processing unit may cause the computer device 10 to control the one or more manufacturing devices 60, 70 to manufacture the one or more additional physical tool heads using the second manufacturing data provided for controlling the manufacturing of the additional physical tool heads.

For example, the manufacturing system 11 may comprise a manufacturing device in form of a machining device 70 controlled by the computer device 10. The machining device 70 may be configured to machining a blank 76 using one or more machining tools 72. The blank 76 of raw material 78, may be provided using one or more holding devices 74 and cut into a desired shape and size of the element to be manufactured, e.g., a physical preparation guide 161 and/or an additional physical tool head. The machining tool 72 may, e.g., be a milling tool. For manufacturing physical preparation guides 161, the raw material 78 may, e.g., be a plastic. In particular for manufacturing additional physical tool heads, the raw material 78 may, e.g., be a metal or a metal alloy.

For example, the manufacturing system 11 may comprise a manufacturing device in form of a three-dimensional (3D) printing device 60. The 3D printing device 60 may be controlled by the computer device 10 and configured to print an element to be manufactured, e.g., a physical preparation guide 161 and/or an additional physical tool head. The 3D printing device 60 may comprise a printing element 62 configured to generate the respective element, like the treatment element 120, layer by layer. The printing element 62 may, e.g., comprise a nozzle configured for distributing printing material.

In case the element to be manufactured using the 3D printing device 60 is made using metal or metal alloys, like an additional physical tool head, the 3D printing device 60 may, e.g., be configured for executing selective laser sintering, laser melting and/or electron beam melting. Selective laser sintering uses a laser for sintering a powdered material, aiming the laser automatically at points in space defined by a three-dimensional digital model of the element to be printed. The laser energy may result in a local sintering of the powdered material, binding the material together to create a solid structure. For example, the printing element 62 of the 3D printing device 60 may comprise a laser and/or a distributing device for distributing the powdered material. In case of laser melting, the laser is used for locally melting the powdered material, binding the material together to create a solid structure. Selective electron beam melting uses an electron beam for melting a powdered material, aiming the electron beam automatically at points in space defined by a three-dimensional digital model of the element to be printed. The beam energy may result in a local melting of the powdered material, binding the material together to create a solid structure. For example, the printing element 62 of the 3D printing device 60 may comprise an electron beam emitter and/or a distributing device for distributing the powdered material.

For example, the three-dimensional digital model of the element to be manufactured, e.g., a three-dimensional digital preparation guide model 160 and/or a three-dimensional digital tool model, may be used as a positive to define a negative of the element to be manufactured in form of a negative three-dimensional digital model. The negative three-dimensional digital model may be used to manufacture, e.g., using machining device 70 or 3D printing device 60, a casting matrix. The casting matrix may be configured for casting the element to be manufactured by inserting casting material into the casting matrix and curing the inserted casting material.

The one or more physical preparation guide models 161 being manufactured may, e.g., be configured as splint to be arranged on the one or more teeth to be prepared. The physical preparation guide models 161 may provide a guidance for a movement of the tool heads of the section. The physical preparation guide models 161 may define boundaries of individual preparation steps to be executed using the individual tool heads of the selection.

The one or more additional physical tool heads being manufactured may, e.g., comprise one or more milling tool heads and/or one or more drilling tool heads.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word “comprising” does not exclude other elements or steps, and the indefinite article “a” or “an” does not exclude a plurality. The mere fact that certain measures are recited in mutually different dependent claims does not indicate that a combination of these measured cannot be used to advantage. Any reference signs in the claims should not be construed as limiting the scope.

A single processor or other unit may fulfill the functions of several items recited in the claims. A computer program may be stored/distributed on a suitable medium, such as an optical storage medium or a solid-state medium supplied together with or as part of other hardware, but may also be distributed in other forms, such as via the Internet or other wired or wireless telecommunication systems.

As will be appreciated by one skilled in the art, aspects of the present invention may be embodied as an apparatus, method, computer program or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a “circuit,” “module” or “system.” Furthermore, aspects of the present invention may take the form of a computer program product embodied in one or more computer readable medium(s) having computer executable code embodied thereon. A computer program comprises the computer executable code or “program instructions”.

Any combination of one or more computer readable medium(s) may be utilized. The computer readable medium may be a computer readable signal medium or a computer readable storage medium. A “computer-readable storage medium" as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. For example, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. A further example of an optical disk may be a Blu-ray disk. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

"Computer memory" or "memory" is an example of a computer-readable storage medium. Computer memory is any memory which is directly accessible to a processor. "Computer storage" or "storage" is a further example of a computer-readable storage medium. Computer storage is any non-volatile computer-readable storage medium. For example, computer storage may also be computer memory or vice versa.

A "processor" as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer device or distributed amongst multiple computer devices. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Generally, the program instructions can be executed on one processor or on several processors. In the case of multiple processors, they can be distributed over several different entities like clients, servers etc. Each processor could execute a portion of the instructions intended for that entity. Thus, when referring to a system or process involving multiple entities, the computer program or program instructions are understood to be adapted to be executed by a processor associated or related to the respective entity.

A "user interface" as used herein is an interface which allows a user or operator to interact with a computer or computer device. A 'user interface' may also be referred to as a 'human interface device'. A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, one or more switches, one or more buttons, and accelerometer are all examples of user interface components which enable the receiving of information or data from an operator.

A GUI element is a data object some of which's attributes specify the shape, layout and/or behavior of an area displayed on a graphical user interface, e.g., a screen. A GUI element can be a standard GUI element such as a button, a text box, a tab, an icon, a text field, a pane, a check-box item or item group or the like. A GUI element can likewise be an image, an alphanumeric character or any combination thereof. At least some of the properties of the displayed GUI elements depend on the data value aggregated on the group of data object said GUI element represents.

Aspects of the present invention are described with reference to flowchart illustrations and/or block diagrams of methods, apparatus (systems) and computer program products. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer-implemented process such that the instructions which execute on the computer or other programmable apparatus provide processes for implementing the functions/acts specified in the flowchart and/or block diagram block or blocks.

Although the invention may have been described in reference to specific examples, it should be understood that the invention is not limited to these examples only and that many variations of these examples may be readily envisioned by the skilled person after having read the present disclosure. The invention may thus further be described without limitation and by way of example only by the following examples. The following examples may contain preferred embodiments. Accordingly, the term “feature combination” as used therein may refer to such a “preferred embodiment”.

1. A computer-implemented method for selecting tool heads for a tooth preparation comprising a removal of tooth material, the method comprising:
   - receiving a three-dimensional digital initial tooth model descriptive of one or more current states of one or more teeth to be prepared;
   - receiving a three-dimensional digital target tooth model descriptive of one or more target states of the respective one or more teeth to be prepared, wherein the one or more target states are to be achieved starting from the one or more current states by preparing the one or more teeth to be prepared comprising the removal of the tooth material from the respective teeth;
   - receiving definitions of tool heads of a plurality of tool heads of a plurality of tool kits defining features of the tool heads of the plurality of tool heads;
   - checking, using the defined features of the tool heads of the plurality of tool heads, for different combinations and sequences of usage of the tool heads of the plurality of tool heads, whether one or more preparation criteria are satisfied;
   - determining a selection of tool heads from the plurality of tool heads and a sequence of usage of the tool heads of the selection for the tooth preparation satisfying the one or more preparation criteria, wherein the determining comprises executing a simulation of the tooth preparation using the tool heads of the selection according to the sequence of usage of the tool heads of the selection, the simulation being executed using the defined features of the respective tool heads of the selection;
   - outputting a result of the simulation comprising a definition of the selection of tool heads and the sequence of usage of the tool heads of the selection.
2. The method of feature combination 1, the definitions of the tool heads of the plurality of tool heads defining one or more of the following features of the tool heads of the plurality of tool heads: shapes of the tool heads, surface structures of the tool heads.
3. The method of any of the previous feature combinations, the simulation of the tooth preparation comprising a determining of preparation trajectories for moving the tool heads of the selection according to the sequence of usage of the tool heads of the selection through the teeth to be prepared.
4. The method of any of the previous feature combinations, the method further comprising executing additional different simulations of the tooth preparation with the different combinations and sequences of usage of the tool heads of the plurality of tool heads using the defined features of the respective tool heads, using the different simulations for the checking, whether one or more preparation criteria are satisfied.
5. The method of any of the previous feature combinations, the one or more preparation criteria comprising one or more first criteria for a preparation time.
6. The method of feature combination 5, the features of the tool heads of the plurality of tool heads being related to approximated preparation times resulting from a usage of the respective tool heads, the checking comprising a checking of the one or more first criteria using the defined features of the tool heads of the plurality of tool heads.
7. The method of any of the previous feature combinations, the one or more preparation criteria comprising one or more second criteria for a precision of the tooth preparation.
8. The method of feature combination 7, the defined features of the tool heads of the plurality of tool heads being related to approximated precisions of the tooth preparation resulting from a usage of the respective tool heads, the checking comprising a checking of the one or more second criteria using the defined features of the tool heads of the plurality of tool heads.
9. The method of any of the previous feature combinations, the method further comprising generating one or more three-dimensional digital preparation guide models for one or more steps of the tooth preparation using the simulation of the tooth preparation with the tool heads of the selection according to the sequence of usage of the tool heads of the selection, the one or more three-dimensional digital preparation guide models defining one or more preparation guides configured to guide a usage of one or more of the tool heads of the selection according to the respective simulation.
10. The method of feature combination 9, one or more of the one or more three-dimensional preparation guides defining one or more intermediate states of the tooth preparation to be achieved using the tool heads of the selection according to the sequence of usage of the tool heads of the selection.
11. The method of any of feature combinations 9 to 10, the method further comprising providing first manufacturing data for controlling a manufacturing of one or more physical preparation guides, the first manufacturing data defining the three-dimensional digital preparation guide models as templates for the physical preparation guides.

12. The method of feature combination 11, the method further comprising manufacturing of the one or more physical preparation guides using the first manufacturing data provided for controlling the manufacturing with the one or more manufactured physical preparation guides being physical copies of the templates defined by the provided first manufacturing data.

13. The method of any of the previous feature combinations, the method further comprising a generating of the three-dimensional digital target tooth model, the generating of the three-dimensional digital target tooth model comprising identifying one or more damaged sections of the one or more teeth of the three-dimensional digital initial tooth model and determining one or more sections of the respective teeth to be removed by the tooth preparation, wherein the determined sections to be removed comprise the one or more identified damaged sections.

14. The method of any of the previous feature combinations, the method further comprising generating and providing control data configured for controlling a robotic device to execute the tooth preparation according to the simulation using the tool heads of the selection according to the sequence of usage of the tool heads of the selection.

15. The method of any of the previous feature combinations, the method further comprising:

in response to a result of the checking, whether the one or more preparation criteria are satisfied, indicating that none of the checked combinations and sequences of usage of the tool heads of the plurality of tool heads satisfies the one or more preparation criteria, determining one or more additional tool heads with features configured to achieve the one or more target states satisfying the one or more preparation criteria, expanding the plurality of tool heads by adding the one or more additional tool heads, re-executing the checking, whether the one or more preparation criteria are satisfied, using the expanded the plurality of tool heads, wherein the determined selection of tool heads from the plurality of tool heads comprising one or more of the one or more additional tool heads.

16. The method of feature combination 15, the method further comprising:

generating one or more additional three-dimensional digital tool models of the one or more additional tool heads, providing second manufacturing data for controlling a manufacturing of one or more additional physical tool heads, the second manufacturing data defining the additional three-dimensional digital tool models as templates for the additional physical tool heads.

17. The method of feature combination 16, the method further comprising manufacturing of the one or more additional physical tool heads using the second manufacturing data provided for controlling the manufacturing with the one or more manufactured additional physical tool heads being physical copies of the templates defined by the provided second manufacturing data.

18. A computer program product for selecting tool heads for a tooth preparation comprising a removal of tooth material, the computer program product comprising a non-transitory computer readable storage medium having program instructions embodied therewith, the program instructions being executable by a processing unit of a computer device to cause the computer device to:

receive a three-dimensional digital initial tooth model descriptive of one or more current states of one or more teeth to be prepared;

receive a three-dimensional digital target tooth model descriptive of one or more target states of the respective one or more teeth to be prepared, wherein the one or more target states are to be achieved starting from the one or more current states by preparing the one or more teeth to be prepared comprising the removal of the tooth material from the respective teeth;

receive definitions of tool heads of a plurality of tool heads of a plurality of tool kits defining features of the tool heads of the plurality of tool heads;

check, using the defined features of the tool heads of the plurality of tool heads, for different combinations and sequences of usage of the tool heads of the plurality of tool heads, whether one or more preparation criteria are satisfied;

determine a selection of tool heads from the plurality of tool heads and a sequence of usage of the tool heads of the selection for the tooth preparation satisfying the one or more preparation criteria, wherein the determining comprises executing a simulation of the tooth preparation using the tool heads of the selection according to the sequence of usage of the tool heads of the selection, the simulation being executed using the defined features of the respective tool heads of the selection;

output a result of the simulation comprising a definition of the selection of tool heads and the sequence of usage of the tool heads of the selection.

19. A computer program for selecting tool heads for a tooth preparation comprising a removal of tooth material, the computer program comprising program instructions being executable by a processing unit of a computer device to cause the computer device to:

receive a three-dimensional digital initial tooth model descriptive of one or more current states of one or more teeth to be prepared;

receive a three-dimensional digital target tooth model descriptive of one or more target states of the respective one or more teeth to be prepared, wherein the one or more target states are to be achieved starting from the one or more current states by preparing the one or more teeth to be prepared comprising the removal of the tooth material from the respective teeth;

receive definitions of tool heads of a plurality of tool heads of a plurality of tool kits defining features of the tool heads of the plurality of tool heads;

check, using the defined features of the tool heads of the plurality of tool heads, for different combinations and sequences of usage of the tool heads of the plurality of tool heads, whether one or more preparation criteria are satisfied;

determine a selection of tool heads from the plurality of tool heads and a sequence of usage of the tool heads of the selection for the tooth preparation satisfying the one or more preparation criteria, wherein the determining comprises executing a simulation of the tooth preparation using the tool heads of the selection according to the sequence of usage of the tool heads of the selection, the simulation being executed using the defined features of the respective tool heads of the selection;

output a result of the simulation comprising a definition of the selection of tool heads and the sequence of usage of the tool heads of the selection.

20. A computer device for selecting tool heads for a tooth preparation comprising a removal of tooth material, the computer device comprising a processing unit and a memory storing program instructions executable by the processing unit, execution of the program instructions by the processing unit causing the computer device to:

receive a three-dimensional digital initial tooth model descriptive of one or more current states of one or more teeth to be prepared;

receive a three-dimensional digital target tooth model descriptive of one or more target states of the respective one or more teeth to be prepared, wherein the one or more target states are to be achieved starting from the one or more current states by preparing the one or more teeth to be prepared comprising the removal of the tooth material from the respective teeth;

receive definitions of tool heads of a plurality of tool heads of a plurality of tool kits defining features of the tool heads of the plurality of tool heads;

check, using the defined features of the tool heads of the plurality of tool heads, for different combinations and sequences of usage of the tool heads of the plurality of tool heads, whether one or more preparation criteria are satisfied;

determine a selection of tool heads from the plurality of tool heads and a sequence of usage of the tool heads of the selection for the tooth preparation satisfying the one or more preparation criteria, wherein the determining comprises executing a simulation of the tooth preparation using the tool heads of the selection according to the sequence of usage of the tool heads of the selection, the simulation being executed using the defined features of the respective tool heads of the selection;

output a result of the simulation comprising a definition of the selection of tool heads and the sequence of usage of the tool heads of the selection.

21. A tool system comprising the computer device of feature combination 20, the tool system further comprising one or more of the tool kits of the plurality of tool kits and a robotic device, execution of the program instructions by the processing unit further causing the computer device to:

generate and provide control data configured for controlling the robotic device to execute the tooth preparation according to the simulation using the tool heads of the selection according to the sequence of usage of the tool heads of the selection.

22. A manufacturing system comprising the computer device of feature combination 20, the manufacturing system further comprising one or more manufacturing devices configured to manufacture one or more preparation guides configured to guide a usage of the tool heads of the selection according to the simulation of the tooth preparation, execution of the program instructions by the processing unit further causing the computer device to:

generate one or more three-dimensional digital preparation guide models for one or more steps of the tooth preparation using the simulation of the tooth preparation, the one or more three-dimensional digital preparation guide models defining the one or more preparation guides, provide first manufacturing data for controlling a manufacturing of one or more physical preparation guides, the first manufacturing data defining the three-dimensional digital preparation guide models as templates for the physical preparation guides, control the one or more manufacturing devices to manufacture the one or more physical preparation guides using the first manufacturing data provided for controlling the manufacturing with the manufactured physical preparation guides being physical copies of the templates defined by the first manufacturing data provided.

23. The manufacturing system of feature combination 22, the one or more manufacturing devices of the manufacturing system further being configured for manufacturing one or more additional physical tool heads, execution of the program instructions by the processing unit further causing the computer device to:

in response to a result of the checking, whether one or more preparation criteria are satisfied, indicating that none of the checked combinations and sequences of usage of the tool heads of the plurality of tool heads satisfies the one or more preparation criteria, determine one or more additional tool heads with features configured to achieve the one or more target states satisfying the one or more preparation criteria, expand the plurality of tool heads by adding the one or more additional tool heads, the determined selection of tool heads from the plurality of tool heads comprising the one or more additional tool heads, generate one or more additional three-dimensional digital tool models of the one or more additional tool heads, provide second manufacturing data for controlling a manufacturing of one or more additional physical tool heads, the second manufacturing data defining the additional three-dimensional digital tool models as templates for the additional physical tool heads, control the one or more manufacturing devices to manufacture the one or more additional physical tool heads using the second manufacturing data provided for controlling the manufacturing with the manufactured additional physical tool heads being physical copies of the templates defined by the second manufacturing data provided.

REFERENCE SIGNS LIST

10 computer device
11 manufacturing system
14 external device
16 processing unit
18 bus
20 network adapter
22 I/O interface
24 display

28 memory
30 RAM
32 cache
34 storage system
40 program
42 program module
50 user interface
52 control elements
54 hardware device
56 keyboard
58 mouse
59 scanner
60 3D printing device
62 printing element
70 machining device
72 machining tool
74 holding device
76 blank
78 raw material
100 3D digital initial tooth model
102 3D digital target tooth model
103 preparation section
104 tooth to be prepared
105 preparation boundary
106 prepared tooth section
107 3D digital gingiva model
108 prepared tooth
110 tool kit
112 tool head
114 cutting edge
121 feather edge
122 knife edge
123 chamfer edge
124 bevel edge
125 shoulder edge
126 beveled shoulder edge
130 3D digital dental restoration model
132 minimum material thickness
134 insertion direction
136 section to be removed
140 dental restoration element
142 prepared molar tooth
150 defect
160 3D digital preparation guide model
161 physical preparation guide
162 guiding element
170 robotic device

The invention claimed is:

1. A computer-implemented method for selecting tool heads for a tooth preparation comprising a removal of tooth material, the method comprising:

receiving a three-dimensional digital initial tooth model descriptive of one or more current states of one or more teeth to be prepared;

receiving a three-dimensional digital target tooth model descriptive of one or more target states of the respective one or more teeth to be prepared, wherein the one or more target states are to be achieved starting from the one or more current states by preparing the one or more teeth to be prepared comprising the removal of the tooth material from the respective teeth;

receiving definitions of tool heads of a plurality of tool heads of a plurality of tool kits defining features of the tool heads of the plurality of tool heads;

checking, using the defined features of the tool heads of the plurality of tool heads, for different combinations and sequences of usage of the tool heads of the plurality of tool heads, whether one or more preparation criteria are satisfied, the one or more preparation criteria comprising one or more first criteria for a preparation time, the features of the tool heads of the plurality of tool heads being related to approximated preparation times resulting from a usage of the respective tool heads, the checking comprising a checking of the one or more first criteria using the defined features of the tool heads of the plurality of tool heads;

determining a selection of tool heads from the plurality of tool heads and a sequence of usage of the tool heads of the selection for the tooth preparation satisfying the one or more preparation criteria, wherein the determining comprises executing a simulation of the tooth preparation using the tool heads of the selection according to the sequence of usage of the tool heads of the selection, the simulation being executed using the defined features of the respective tool heads of the selection;

outputting a result of the simulation comprising a definition of the selection of tool heads and the sequence of usage of the tool heads of the selection.

2. The method of claim 1, the definitions of the tool heads of the plurality of tool heads defining one or more of the following features of the tool heads of the plurality of tool heads: shapes of the tool heads, surface structures of the tool heads.

3. The method of claim 1, the simulation of the tooth preparation comprising a determining of preparation trajectories for moving the tool heads of the selection according to the sequence of usage of the tool heads of the selection through the teeth to be prepared.

4. The method of claim 1, the method further comprising executing additional different simulations of the tooth preparation with the different combinations and sequences of usage of the tool heads of the plurality of tool heads using the defined features of the respective tool heads, using the different simulations for the checking, whether one or more preparation criteria are satisfied.

5. The method of claim 1, the one or more preparation criteria comprising one or more second criteria for a precision of the tooth preparation.

6. The method of claim 5, the defined features of the tool heads of the plurality of tool heads being related to approximated precisions of the tooth preparation resulting from a usage of the respective tool heads, the checking comprising a checking of the one or more second criteria using the defined features of the tool heads of the plurality of tool heads.

7. The method of claim 1, the method further comprising generating one or more three-dimensional digital preparation guide models for one or more steps of the tooth preparation using the simulation of the tooth preparation with the tool heads of the selection according to the sequence of usage of the tool heads of the selection, the one or more three-dimensional digital preparation guide models defining one or more preparation guides configured to guide a usage of one or more of the tool heads of the selection according to the respective simulation.

8. The method of claim 7, one or more of the one or more three-dimensional preparation guides defining one or more intermediate states of the tooth preparation to be achieved using the tool heads of the selection according to the sequence of usage of the tool heads of the selection.

9. The method of claim 7, the method further comprising providing first manufacturing data for controlling a manufacturing of one or more physical preparation guides, the first manufacturing data defining the three-dimensional digital preparation guide models as templates for the physical preparation guides.

10. The method of claim 9, the method further comprising manufacturing of the one or more physical preparation guides using the first manufacturing data provided for controlling the manufacturing with the one or more manufactured physical preparation guides being physical copies of the templates defined by the provided first manufacturing data.

11. The method of claim 1, the method further comprising a generating of the three-dimensional digital target tooth model, the generating of the three-dimensional digital target tooth model comprising identifying one or more damaged sections of the one or more teeth of the three-dimensional digital initial tooth model and determining one or more sections of the respective teeth to be removed by the tooth preparation, wherein the determined one or more sections to be removed comprise the one or more identified one or more damaged sections.

12. The method of claim 1, the method further comprising generating and providing control data configured for controlling a robotic device to execute the tooth preparation according to the simulation using the tool heads of the selection according to the sequence of usage of the tool heads of the selection.

13. The method of claim 1, the method further comprising:

in response to a result of the checking, whether the one or more preparation criteria are satisfied, indicating that none of the checked combinations and sequences of usage of the tool heads of the plurality of tool heads satisfies the one or more preparation criteria, determining one or more additional tool heads with features configured to achieve the one or more target states satisfying the one or more preparation criteria, expanding the plurality of tool heads by adding the one or more additional tool heads, re-executing the checking, whether the one or more preparation criteria are satisfied, using the expanded the plurality of tool heads, wherein the determined selection of tool heads from the plurality of tool heads comprising one or more of the one or more additional tool heads.

14. The method of claim 13, the method further comprising:

generating one or more additional three-dimensional digital tool models of the one or more additional tool heads, providing second manufacturing data for controlling a manufacturing of one or more additional physical tool heads, the second manufacturing data defining the additional three-dimensional digital tool models as templates for the additional physical tool heads.

15. The method of claim 14, the method further comprising manufacturing of the one or more additional physical tool heads using the second manufacturing data provided for controlling the manufacturing with the one or more manufactured additional physical tool heads being physical copies of the templates defined by the provided second manufacturing data.

16. A computer program product for selecting tool heads for a tooth preparation comprising a removal of tooth material, the computer program product comprising a non-transitory computer readable storage medium having program instructions embodied therewith, the program instructions being executable by a processing unit of a computer device to cause the computer device to:

receive a three-dimensional digital initial tooth model descriptive of one or more current states of one or more teeth to be prepared;

receive a three-dimensional digital target tooth model descriptive of one or more target states of the respective one or more teeth to be prepared, wherein the one or more target states are to be achieved starting from the one or more current states by preparing the one or more teeth to be prepared comprising the removal of the tooth material from the respective teeth;

receive definitions of tool heads of a plurality of tool heads of a plurality of tool kits defining features of the tool heads of the plurality of tool heads;

check, using the defined features of the tool heads of the plurality of tool heads, for different combinations and sequences of usage of the tool heads of the plurality of tool heads, whether one or more preparation criteria are satisfied, the one or more preparation criteria comprising one or more first criteria for a preparation time, the features of the tool heads of the plurality of tool heads being related to approximated preparation times resulting from a usage of the respective tool heads, the checking comprising a checking of the one or more first criteria using the defined features of the tool heads of the plurality of tool heads;

determine a selection of tool heads from the plurality of tool heads and a sequence of usage of the tool heads of the selection for the tooth preparation satisfying the one or more preparation criteria, wherein the determining comprises executing a simulation of the tooth preparation using the tool heads of the selection according to the sequence of usage of the tool heads of the selection, the simulation being executed using the defined features of the respective tool heads of the selection;

output a result of the simulation comprising a definition of the selection of tool heads and the sequence of usage of the tool heads of the selection.

17. A computer device for selecting tool heads for a tooth preparation comprising a removal of tooth material, the computer device comprising a processing unit and a memory storing program instructions executable by the processing unit, execution of the program instructions by the processing unit causing the computer device to:

receive a three-dimensional digital initial tooth model descriptive of one or more current states of one or more teeth to be prepared;

receive a three-dimensional digital target tooth model descriptive of one or more target states of the respective one or more teeth to be prepared, wherein the one or more target states are to be achieved starting from the one or more current states by preparing the one or more teeth to be prepared comprising the removal of the tooth material from the respective teeth;

receive definitions of tool heads of a plurality of tool heads of a plurality of tool kits defining features of the tool heads of the plurality of tool heads;

check, using the defined features of the tool heads of the plurality of tool heads, for different combinations and sequences of usage of the tool heads of the plurality of tool heads, whether one or more preparation criteria are satisfied, the one or more preparation criteria comprising one or more first criteria for a preparation time, the features of the tool heads of the plurality of tool heads being related to approximated preparation times resulting from a usage of the respective tool heads, the checking comprising a checking of the one or more first criteria using the defined features of the tool heads of the plurality of tool heads;

determine a selection of tool heads from the plurality of tool heads and a sequence of usage of the tool heads of the selection for the tooth preparation satisfying the one or more preparation criteria, wherein the determining comprises executing a simulation of the tooth preparation using the tool heads of the selection according to the sequence of usage of the tool heads of the selection, the simulation being executed using the defined features of the respective tool heads of the selection;

output a result of the simulation comprising a definition of the selection of tool heads and the sequence of usage of the tool heads of the selection.

18. A tool system comprising the computer device of claim 17, the tool system further comprising one or more of the tool kits of the plurality of tool kits and a robotic device, execution of the program instructions by the processing unit further causing the computer device to:

generate and provide control data configured for controlling the robotic device to execute the tooth preparation according to the simulation using the tool heads of selection according to the sequence of usage of the tool heads of the selection.

* * * * *